US012642874B2

(12) United States Patent
Chavez et al.

(10) Patent No.: US 12,642,874 B2
(45) Date of Patent: Jun. 2, 2026

(54) METHODS OF TREATING EYE DISEASES

(71) Applicant: Visgenx, Inc., Rancho Mission Viejo, CA (US)

(72) Inventors: Christopher Chavez, Santa Cruz, CA (US); Martin Emanuele, San Diego, CA (US)

(73) Assignee: Visgenx, Inc., Rancho Mission Viejo, CA (US)

( * ) Notice: Subject to any disclaimer, the term of this patent is extended or adjusted under 35 U.S.C. 154(b) by 0 days.

(21) Appl. No.: 18/471,187

(22) Filed: Sep. 20, 2023

(65) Prior Publication Data

US 2024/0066151 A1     Feb. 29, 2024

Related U.S. Application Data

(60) Division of application No. 17/821,976, filed on Aug. 24, 2022, now Pat. No. 11,793,890, which is a continuation of application No. PCT/US2021/055648, filed on Oct. 19, 2021.

(60) Provisional application No. 63/104,169, filed on Oct. 22, 2020.

(51) Int. Cl.
| | |
|---|---|
| *A61K 48/00* | (2006.01) |
| *A61K 45/06* | (2006.01) |
| *A61P 27/02* | (2006.01) |

(52) U.S. Cl.
CPC .......... *A61K 48/0066* (2013.01); *A61K 45/06* (2013.01); *A61K 48/0075* (2013.01); *A61P 27/02* (2018.01)

(58) Field of Classification Search
None
See application file for complete search history.

(56) References Cited

U.S. PATENT DOCUMENTS

| | | |
|---|---|---|
| 2009/0203787 A1 | 8/2009 | Anderson et al. |
| 2012/0316112 A1 | 12/2012 | Bartus et al. |
| 2017/0211102 A1 | 7/2017 | Giver et al. |
| 2019/0374653 A1 | 12/2019 | Skowonska-Krawczyk et al. |
| 2020/0023015 A1 | 1/2020 | Herzberg et al. |

FOREIGN PATENT DOCUMENTS

| | | |
|---|---|---|
| WO | WO 2017/191274 | 11/2017 |
| WO | WO 2019/241728 A1 | 12/2019 |

OTHER PUBLICATIONS

Castro et al. BioDrugs, 2024, vol. 38, pp. 73-93 (Year: 2024).*
PCT International Search Report and Written Opinion, Mar. 16, 2022, 20 pages.
Chen et al., "The lipid elongation enzyme ELOVL2 is a molecular regulator of aging in the retina." Aging Cell. Feb. 2020;19(2):e13100.
Gallego et al., "Non-viral vectors based on cationic niosomes and minicircle DNA technology enhance gene delivery efficiency for biomedical applications in retinal disorders." *Nanomedicine: Nanotechnology, Biology and Medicine 17* (2019): 308-318.
Liu et al., BFV45869 and alignment, 2007.
Gao et al., ABR62759 and alignment, 2019.

* cited by examiner

*Primary Examiner* — Celine X Qian
(74) *Attorney, Agent, or Firm* — KNOBBE, MARTENS, OLSON & BEAR, LLP

(57) ABSTRACT

Disclosed herein are therapeutic agents capable of increasing the expression level of ELOVL2. Also described herein are therapeutic agents that reduce or slow an aging phenotype. Methods for treating age-related eye diseases or conditions are also provided. Methods for treating an age-related eye disease or condition in a subject by administering one or more therapeutic agents are provided.

13 Claims, 12 Drawing Sheets

Specification includes a Sequence Listing.

ELOVL2 Variant Comparison: GFP Expression in
APRE19 Cells 48 hrs Post Transfection

CV1

WTMC

WT

CMV-CV1

ELOVL2 Western Blot
(20X over AREPE19 and 10X over WT)

1. ARPE19-WT 2. ELOVL2-KO 3. EF1a-WT 4. EF1a-CV1
5. EF1a-CV4 6. CMV-CV1 7. CMV-CV4 8. CMV-T-CV4

Dose Response MFI of ARPE19 Cells Transduced with AAV8-CMVT-CV4-GFP

METHODS OF TREATING EYE DISEASES

This application is divisional application of U.S. patent application Ser. No. 17/821,976 filed on Aug. 24, 2022, which is a continuation application of international PCT Application No. PCT/US2021/055648, filed on Oct. 19, 2021, which claims the benefit of priority to U.S. Provisional Application No. 63/104,169, filed on Oct. 22, 2020. All of the foregoing applications are fully incorporated herein by reference in their entireties for all purposes.

FIELD OF THE DISCLOSURE

The present disclosure relates to the fields of biochemistry and medicine. More particularly, the present disclosure relates to methods and compositions useful for ELOVL2 gene therapy to treat eye diseases.

BACKGROUND

Long chain and very long chain polyunsaturated fatty acids (LC-PUFA and VLC-PUFA respectively) have been demonstrated to be critically important in multiple biological processes. They are widely accepted to act in multiple tissues as: 1) energy sources, 2) structural membrane components, and 3) key mediators in signal transduction pathways.

LC-PUFA cannot be synthesized de novo by humans and dietary sources of shorter chain fatty acid precursors are necessary for LC-PUFA tissue biosynthesis. The shorter chain fatty acids are "elongated" in a process where 2 carbons are added in a step-by-step manner by the action of various elongase enzymes. One such elongase ELOVL2 has been shown to play an essential role in the conversion of docosapentanoic acid (DPA) (22:5n-3) to DHA (22:6n-3).

REFERENCE TO SEQUENCE LISTING

The present application is filed with a Sequence Listing in Electronic format. The Sequence Listing is provided as a file entitled VGENX003SEQLIST.xml, created Aug. 23, 2022, which is approximately 48 kb in size. The information in the electronic format of the sequence listing is incorporated herein by reference in its entirety.

SUMMARY OF THE DISCLOSURE

The present disclosure provides methods of modifying, maintaining, or increasing tissue levels of ELOVL2 enzyme in a subject. In some embodiments, the method includes administering the subject a composition comprising an optimized polynucleotide sequence that increases the tissue levels of ELOVL2. In some embodiments, the optimized polynucleotide sequence comprises an optimized codon of SEQ ID NO: 2 or a sequence exhibiting at least 95% identity to SEQ ID NO: 2. In some embodiments, the optimized polynucleotide sequence comprises an optimized codon of SEQ ID NO: 3 or a sequence exhibiting at least 95% identity to SEQ ID NO: 3. In some embodiments, the polynucleotide sequence further comprises a promoter, an enhancer, an inverted terminal repeats (ITR), polyadenylation signal, a signal sequence, or a combination thereof which can include but are not limited to SEQ ID NOs: 4, 5, 6, 7, 8, 9, 11, 12, and 15. In some embodiments, the optimized polynucleotide sequence further comprises a viral capsid or an envelope or a non-viral delivery system. In some embodiments, the optimized polynucleotide sequence further comprises both a viral capsid and an envelope or a non-viral delivery system. In some embodiments, the viral capsid and envelope are independently selected from an adeno-associated virus-based (AAV), adenovirus-based, alphavirus-based, herpesvirus-based, retrovirus-based, lentivirus-based, or vaccinia virus-based. In some embodiments, the viral capsid and envelope can include but are not limited to SEQ ID NOs.: 19, 20, 21, and 22. In some embodiments, the optimized polynucleotide sequence is in a non-viral delivery system where it may be associated with or encapsulated in synthetic polymeric micro-particles. In some embodiments the optimized polynucleotide sequence is in a DNA minicircle format. In some embodiments, the method further comprises administering an additional therapeutic agent. In some embodiments, the additional therapeutic agent is an anti-complement agent or an anti-VEGF agent. In some embodiments, the additional therapeutic agent is a corticosteroid, an anti-inflammation agent, a demethylating agent, or a combination thereof. In some embodiments, the demethylating agent is decitabine. In some embodiments, the subject is a human.

The disclosure further provides methods of reducing or slowing-down an aging phenotype in a subject in need thereof. In some embodiments, the method includes administering the subject a composition comprising an optimized polynucleotide sequence that increases the tissue levels of ELOVL2 enzyme. In some embodiments, the optimized polynucleotide sequence comprises a polynucleotide sequence of SEQ ID NO: 2 or a sequence exhibiting at least 95% identity to SEQ ID NO: 2. In some embodiments, the optimized polynucleotide sequence comprises a polynucleotide sequence of SEQ ID NO: 3 or a sequence exhibiting at least 95% identity to SEQ ID NO: 3. In some embodiments, the polynucleotide sequence further comprises a promoter, an enhancer, an inverted terminal repeats (ITR), polyadenylation signal, a signal sequence, or a combination thereof which can include but are not limited to SEQ ID NO.s: 4, 5, 6, 7, 8, 9, 11, 12, and 15. In some embodiments, the optimized polynucleotide sequence further comprises a viral capsid or an envelope or a non-viral delivery system. In some embodiments, the optimized polynucleotide sequence further comprises a viral capsid and an envelope or a non-viral delivery system. In some embodiments, the viral capsid and envelope are each independently selected from adeno-associated virus-based (AAV), adenovirus-based, alphavirus-based, herpesvirus-based, retrovirus-based, lentivirus-based, or vaccinia virus-based. In some embodiments the viral capsid and envelope can include but are not limited to SEQ ID NOs: 19, 20, 21, and 22. In some embodiments, the optimized polynucleotide sequence is in a non-viral delivery system where it may be associated with or encapsulated in synthetic polymeric micro-particles. In some embodiments the optimized polynucleotide sequence is in a DNA minicircle format.

The disclosure also provides a method of treating, ameliorating or preventing an age-related eye disease or condition. In some embodiments, the method includes administering the subject a composition comprising an optimized polynucleotide sequence that increases the tissue levels of ELOVL2. In some embodiments, the optimized polynucleotide sequence comprises a polynucleotide sequence of SEQ ID NO: 2 or a sequence exhibiting at least 95% identity to SEQ ID NO: 2. In some embodiments, the optimized polynucleotide sequence comprises a polynucleotide sequence of SEQ ID NO: 3 or a sequence exhibiting at least 95% identity to SEQ ID NO: 3. In some embodiments, the optimized polynucleotide sequence is in a vector. In some embodiments, the polynucleotide sequence further comprises a promoter, an enhancer, an inverted terminal repeats (ITR), polyadenylation signal, a signal sequence, or a combination thereof which can include but are not limited to SEQ ID NOs: 4, 5, 6, 7, 8, 9, 11, 12, and 15. In some embodiments, the optimized polynucleotide sequence further comprises a viral capsid or an envelope or non-viral delivery system. In some embodiments, the optimized polynucleotide sequence further comprises a viral capsid and an envelope or a non-viral delivery system. In some embodiments, the viral capsid or envelope are each independently selected from adeno-associated virus-based (AAV), adeno-virus-based, alphavirus-based, herpesvirus-based, retrovirus-based, lentivirus-based, or vaccinia virus-based. In some embodiments the viral capsid and envelope can include but are not limited to SEQ ID NOs 19, 20, 21, and 22. In some embodiments, the optimized polynucleotide sequence is in a non-viral delivery system where it may be associated with or encapsulated in synthetic polymeric micro-particles. In some embodiments, the optimized polynucleotide sequence is in a DNA minicircle format. In some embodiments, the composition is administered to the eye by an intravitreal, subretinal, subconjunctival, subtenon, or posterior juxtascleral route. In some embodiments, the age-related eye disease is age-related macular degeneration (AMD), diabetic eye disease, glaucoma, low vision or dry eye.

The present disclosure also provides for a composition comprising an optimized polynucleotide sequence of SEQ ID NO: 2 or a sequence exhibiting at least 95% identity to SEQ ID NO: 2 and a vector. The present disclosure also provides for a composition comprising an optimized polynucleotide sequence of SEQ ID NO: 3 or a sequence exhibiting at least 95% identity to SEQ ID NO: 3 and a vector. In some embodiments, the composition further comprises at least one of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO 15. In some embodiments, the optimized polynucleotide sequence is a minicircle format. In some embodiments, the optimized polynucleotide sequence further comprises a capsid or an envelope each independently selected from adeno-associated virus, adenovirus, alphavirus, a herpesvirus, a retrovirus, a lentivirus-based vector, or a vaccinia virus. In some embodiments, the capsid and envelope is from an adeno-associated virus (AAV). In some embodiments, the optimized polynucleotide sequence further comprises a promoter, an enhancer, an intron, an inverted terminal repeats (ITR), a capsid, an envelope, polyadenylation signal, a signal sequence, or a combination thereof. In some embodiments, the composition further comprises an additional therapeutic agent. In some embodiments, the additional therapeutic agent is an anti-complement agent or an anti-VEGF agent. In some embodiments, the additional therapeutic agent is decitabine. In some embodiments, the composition is formulated for intravitreal administration.

BRIEF DESCRIPTION OF THE DRAWINGS

In addition to the features described herein, additional features and variations will be readily apparent from the following descriptions of the drawings and exemplary embodiments. It is to be understood that these drawings depict typical embodiments, and are not intended to be limiting in scope.

FIG. 3 is an image that illustrates the same ARPE19 cells transfected with the ELOVL2/GFP expression constructs as in FIG. 2. ELOVL2/GFP expression is highest in the CMV-CV1 construct compared to those using the EF1a promoter.

DETAILED DESCRIPTION

Figure 1:
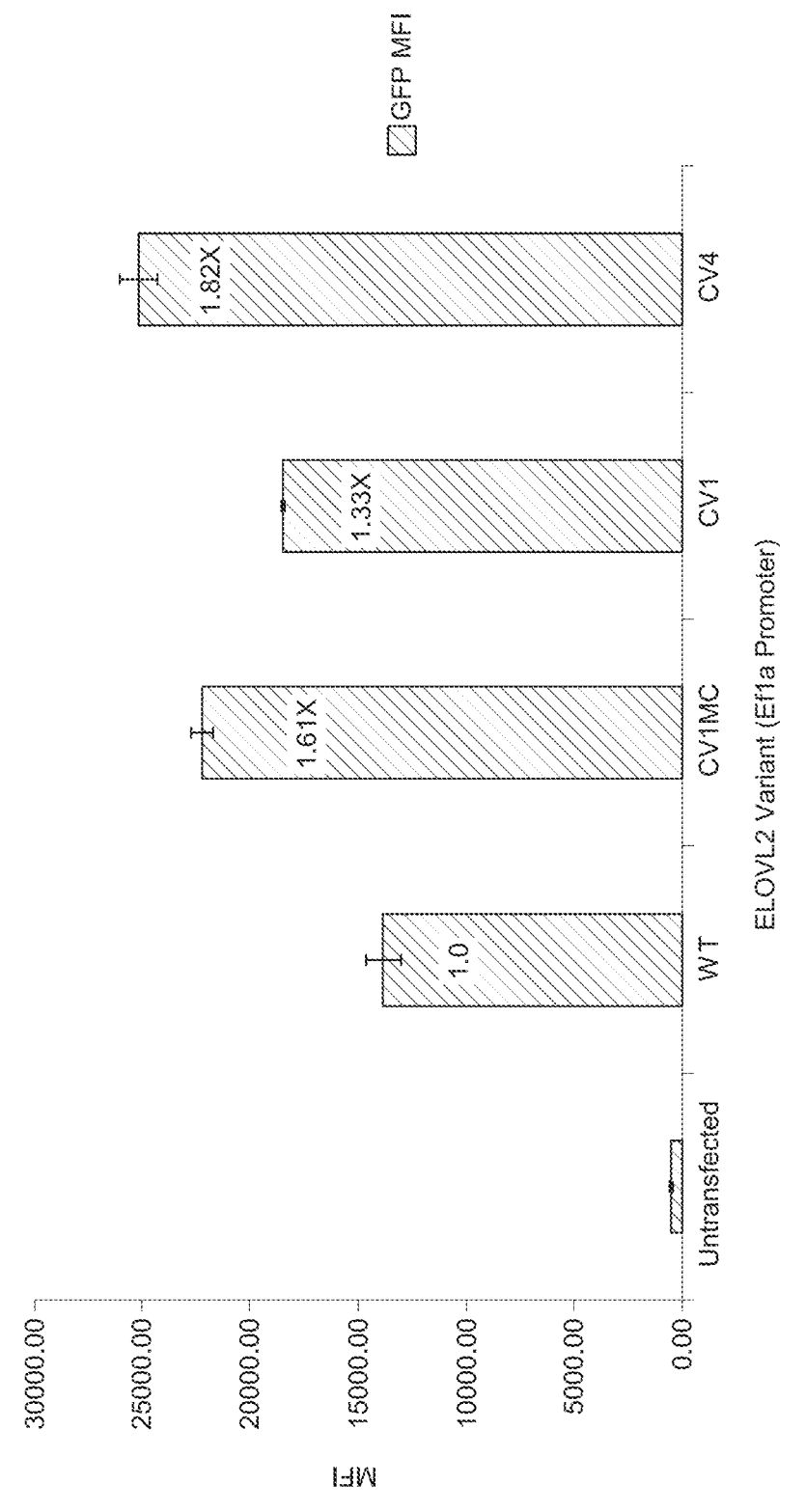
FIG. 1 is a bar graph that illustrates expression of ELOVL2 protein linked to green fluorescent protein (GFP) ("ELOVL2/GFP") in constructs in ARPE19 cells by measuring mean fluorescent intensity (MFI). The cells were transfected with different ELOVL2/GFP expression constructs, including wild type (wt)—SEQ ID NO. 1, codon variant 1 plasmid (CV1)—SEQ ID NO. 2, codon variant 1 minicircle (CV1MC), and codon variant 4 (CV4)—SEQ ID NO. 3. These constructs all used the human EF1a promoter to express the ELOVL2 gene.

ELOVL fatty acid elongase 2 (ELOVL2) is a gene that encodes a transmembrane protein of the same name involved in catalyzing the rate-limiting step of the long-chain fatty acids elongation cycle. Studies in ELOVL2 knockdown mice suggest that ELOVL2 is essential for LC-PUFA and VLC-PUFA homeostasis. ELOVL2 genetic knock-down and knock-out animals show significant pathologies including reproductive sterility, ocular abnormalities, metabolic dysfunction, cognitive impairment and increased cellular aging. It has been observed that during aging the expression of ELOVL2 declines. This loss in ELOVL2 expression (and consequent reduction in ELOVL2 enzyme) may be due to an age related increase in methylation of CPG rich segments in the ELOVL2 gene promotor.

Accordingly, embodiments of the disclosure relate to methods and compositions for increasing ELOVL2 enzyme concentration in tissues where ELOVL2 gene expression has declined. In some embodiments, the disclosure relates to methods for increasing ELOVL2 gene expression using ELOVL2 gene therapy within the eye. In some embodiments, the methods represent an improved therapeutic strategy. In some embodiments, methods for treating vision loss and other aging related dysfunctions using ELOVL2 gene therapy are provided herein. In some embodiments, specific genetic constructs optimized for expression in the target tissue are provided herein. In some embodiments, the gene constructs are optimized to express more highly in human retina cells as compared to expression of the wild-type gene in retina cells.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

The articles "a" and "an" are used herein to refer to one or to more than one (for example, to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In some embodiments, the "purity" of any given agent (e.g., antibody, polypeptide binding agent) in a composition may be specifically defined. For embodiments, certain compositions may comprise an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

As used herein, the terms "function" and "functional" and the like refer to a biological, enzymatic, or therapeutic function.

The term "isolated" is meant material that is substantially or essentially free from components that normally accompany it in its native state. For example, an "isolated cell" or "isolated population of cells" as used herein, includes a cell or population of cells that has been purified from sample material, including other cells, debris, or extraneous sample material from its naturally-occurring state, Alternatively, an "isolated cell" or "isolated population of cells" and the like, as used herein, includes the in vitro, extracorporeal, or other isolation and/or purification of a cell or population of cells from its natural environment, and from association with other components of the sample or material in which it occurs. In some embodiments, isolated means that the component is not significantly associated with in vivo substances.

As used herein, "subject" means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice, guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

As used herein, "treat," "treatment," or "treating" refers to administering a compound or pharmaceutical formulation to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" also refers to administering treatment to a subject already suffering from a disease or condition.

As used herein "administration" or "administering" refers to routes of introducing a compound or composition provided herein to an individual to perform its intended function. For example, "administration" means both intravitreal injection and injection via non intra-vitreal routes. Non-intravitreal routes can include subconjunctiva injection, subretinal injection, sub-tenon injection, retrobulbar injection and suprachoroidal injection. Additional examples also include gene therapy delivery with or without a delivery device. Other non-intravitreal routes include topical application to the eye and injections at other regions of the body intravenous and subcutaneous injection.

As used herein, "co-administration" and similar terms are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time. In some embodiments, the compounds disclosed herein are co-administered.

As used herein a "pharmaceutical formulation" means a bio-compatible aqueous or non-aqueous solution, suspension, dispersion or other physical form that includes an optimized polynucleotide sequence wherein the optimized polynucleotide sequence is at a concentration suitable for administering an effective amount to a mammalian subject.

As used herein, an "optimized" polynucleotide generally refers to nucleotide sequences that have been optimized for a particular host species by replacing any nucleotides from the wild-type so that the nucleotide sequence performs better in a heterologous environment. In one embodiment, optimized polynucleotide sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence.

Compositions

In some aspects, a composition comprising an optimized polynucleotide sequence is described herein. In some embodiments, the optimized polynucleotide sequence comprises a polynucleotide encoding ELOVL2 or a functionally-active fragment thereof. In some embodiments, the optimized polynucleotide sequence is further formulated as a composition for upregulating ELOVL2 expression. In some embodiments, the optimized polynucleotide sequences comprises an optimized codon of SEQ ID NO: 2. In some embodiments, the optimized polynucleotide sequence comprises an optimized codon of SEQ ID NO: 3.

In some embodiments, the composition further comprises a human ELOVL2 enhancer sequence, CMV promoter, adenovirus tripartite leader sequence, synthetic intron, woodchuck hepatitis posttranscriptional regulatory element, and a human growth hormone polyA sequence. In some embodiments, the composition comprises a nucleotide sequence of at least one of SEQ ID NO: 4, SEQ ID NO: 5, SEQ ID NO: 6, SEQ ID NO: 7, SEQ ID NO: 8, SEQ ID NO: 9, and SEQ ID NO: 12, and SEQ ID NO 15.

In some embodiments, the composition comprises an optimized polynucleotide sequence at least 80%, 85%, 90%, 91%, 92%, 93%, 94%, 95%, 96%, 97%, 98%, or 99% sequence identity to SEQ ID NO: 1. In some embodiments, the composition comprises an optimized polynucleotide sequence at least 80%, 85%, 90%, 91%, 92%, 93%, 94%, 95%, 96%, 97%, 98%, or 99% sequence identity to SEQ ID NO: 2. In some embodiments, the composition comprises an optimized polynucleotide sequence at least 80%, 85%, 90%, 91%, 92%, 93%, 94%, 95%, 96%, 97%, 98%, or 99% sequence identity to SEQ ID NO: 3.

In some embodiments, the optimized polynucleotide sequence administered without a viral capsid or envelope. (i.e. a non-viral delivery system). In some embodiments the non-viral delivery system is based on synthetic polymers that encapsulate the optimized polynucleotide sequence. In some embodiments, a DNA minicircle format is utilized for transferring the optimized polynucleotide sequence. A "minicircle DNA vector" may be referred to as "minicircle vector" or "minicircle" is a small (usually in the range of 3-4 kb, approximately 3-4 kb or usually no larger than 10 kb) circular, episomal plasmid derivative wherein all prokaryotic vector parts (e.g., bacterial origin of replication, genes associated with bacterial propagation of plasmids) have been removed. Since minicircle vectors contain no prokaryotic DNA sequences, they are less likely to be perceived as foreign and destroyed when they are employed as vehicles for transferring transgenes into target mammalian cells. In embodiments, a minicircle DNA vector is a minicircle carrying a transgene expression cassette. In examples, a minicircle DNA vector is a minicircle carrying a transgene expression cassette and does not contain an empty vector without an insert. In one or more embodiments, the nucleotide sequence of a minicircle containing the transgene expression cassette comprises SEQ ID NO: 2 or SEQ ID NO: 3.

Minicircle vectors are prepared using a two-step procedure. Firstly, a full-size parental plasmid containing bacterial sequences and transgene is produced in, for example, *Escherichia coli*. While the parental plasmid is still inside the *E. coli* host, the expression of a site-specific recombinase is induced and the prokaryotic or bacterial bone is excised by the enzyme at the recombinase recognition sites. Examples of site-specific recombinases include Tyr- and Ser-recombinases such as Cre recombinase, Flp recombinase, ParA resolvase and PhiC31 integrase. The resulting minicircle vector is recovered by capillary gel electrophoresis. An example of suitable materials, techniques, approaches, and methods are described in U.S. Pat. No. 8,236,548 which is hereby incorporated by reference in its entirety. Further description may be found in Kay et al, A Robust System for Production of Minicircle DNA Vectors, Nature Biotechnology, 2010 28:1287-1289, which is hereby incorporated by reference in its entirety.

In some embodiments, the optimized polynucleotide further comprises a capsid or an envelope. In some embodiments, the optimized polynucleotide further comprises both a capsid and an envelope. In some embodiments, the capsid is AAV serotype 1 based (AAV1), AAV-serotype 2 based (AAV2), AAV serotype 3 based (AAV3), AAV serotype 4 based (AAV4), AAV serotype 5 based (AAV5), AAV serotype 6 based (AAV6), AAV serotype 7 based (AAV7), AAV-serotype 8 based (AAV8), AAV serotype 9 based (AAV9), or humanized AAV-based. In some embodiments, the capsid and envelope are each independently selected from adenovirus, alphavirus, herpesvirus, retrovirus, lentivirus, or vaccinia virus based capsid or envelope polynucleotide sequences.

In some embodiments, the vector comprises a cell or tissue-specific promoter such as rhodopsin kinase operatively linked to the polynucleotide described above. In some cases, the cell or tissue-specific promoter is an endogenous promotor specific to the cell type of interest. In other cases, the cell or tissue-specific promoter is an exogenous promotor specific to the cell type of interest.

In some embodiments, the optimized polynucleotide sequence comprises a microbial promoter. In some cases, the microbial promoter is SV40. In other cases, the microbial promoter comprises cytomegalovirus (CMV) immediate-early promoter.

In some embodiments, the optimized polynucleotide sequence comprises an elongation factor 1-alpha (EF1a) promotor.

In some embodiments, the optimized polynucleotide sequence comprises an enhancer, an inverted terminal repeats (ITR), a capsid, polyadenylation signal, a signal sequence, or a combination thereof.

In some embodiments, an optimized polynucleotide sequence may be further modified for expression in a particular organism, depending on that organism's biological constraints. In some embodiments, a polynucleotide comprises a codon optimized for translation in a human cell. For example, SEQ ID NO:2 or SEQ ID NO:3 comprises sequences that have been optimized for upregulating ELOVL2 expression. In some embodiments, the optimized polynucleotide sequence has been optimized for expression in a human cell. In some embodiments, the optimized polynucleotide sequence may further comprise additional mutations resulting in a conservative amino acid substitution and or improved activity or stability of mRNA or the encoded polypeptide. In some embodiments, the optimized polynucleotide include additional mutations resulting in improved stability of the gene or encoded protein in an eye of a subject.

Pharmaceutical Formulations

In some aspects, an optimized polynucleotide sequence further comprises a pharmaceutical formulation. In some embodiments, the optimized polynucleotide sequence in a pharmaceutical formulation comprises SEQ ID NO: 2 or SEQ ID NO: 3.

In some embodiments, the pharmaceutical formulation (e.g., an optimized polynucleotide) may be administered to a subject by multiple administration routes, including but not limited to intravitreal, subretinal, subconjunctival, sub-tenon, posterior juxtascleral route, intravenous, subcutaneous, intramuscular), oral, intranasal, buccal, rectal, or transdermal administration routes. In some embodiments, the composition (e.g., a pharmaceutical formulation) may be formulated for sub-retinal administration.

In some embodiments, the pharmaceutical formulations include, but are not limited to, aqueous solutions or liquid dispersions, self-emulsifying dispersions, solid solutions, suspensions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some embodiments, the pharmaceutical formulations include buffering, tonicity, stabilizing, suspending, stabilizing, solubilizing, whetting, carrier materials, pH adjusting agents, and the like selected on the basis of compatibility with the composition disclosed herein, and the profile properties of the desired dosage form. Carrier agents may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, fatty acids, poloxamers, dextrans, polyethylene glycols, sodium caseinate, soy lecithin, taurocholic acid, phosphotidylcholine, sodium chloride, tricalcium phosphate, dipotassium phosphate, cellulose and cellulose conjugates, sugars, sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995), Hoover, John E., Remington's Pharmaceutical Sciences, Mack Publishing Co., Easton, Pennsylvania 1975, Liberman, H. A. and Lachman, L., Eds., Pharmaceutical Dosage Forms, Marcel Decker, New York, N.Y., 1980, and Pharmaceutical Dosage Forms and Drug Delivery Systems, Seventh Ed. (Lippincott Williams & Wilkins 1999).

In some embodiments, the pharmaceutical formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range.

In some embodiments, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, maltose, glucose, or salts like potassium phosphate, sodium citrate, ammonium sulfate and/or other agents to increase solubility and in vivo stability. In some embodiments, the pharmaceutical formulations further include a diluent. Salts dissolved in buffered solutions (which also can provide pH control or maintenance) are utilized as diluents in the art, including, but not limited to a phosphate buffered saline solution.

Methods of Use

In some aspects, disclosed herein are methods to modify, maintain, or increase tissue levels of ELOVL2 enzyme in a subject in need thereof. In some embodiments, the disclosure relates to methods for increasing ELOVL2 gene expression within the eye. In some embodiments, the disclosure relates to methods for maintaining ELOVL2 gene expression within the eye. In some embodiments, the disclosure relates to modifying ELOVL2 gene expression within the eye. In some embodiments, the method includes administering the subject a composition comprising an optimized polynucleotide sequence that increases the tissue levels of ELOVL2 enzyme. In some embodiments, the optimized polynucleotide sequence comprises SEQ ID NO: 2 or a sequence exhibiting at least 95% identity to SEQ ID NO: 2. In some embodiments, the optimized polynucleotide sequence comprises SEQ ID NO: 3 or a sequence exhibiting at least 95% identity to SEQ ID NO: 3. In some embodiments, the optimized polynucleotide sequence includes a delivery vector. In some embodiments, the vector comprises an adeno associated virus vector, adenovirus-based vector, an alphavirus-based vector, a herpesvirus-based vector, a retrovirus-based vector, a lentivirus-based vector, or a vaccinia virus-based vector. In some embodiments, the optimized polynucleotide sequence may be in a minicircle format. In some embodiments, the composition further comprises a nucleotide sequence of at least one of SEQ ID NO: 2, SEQ ID NO. 3, SEQ ID NO: 4, SEQ ID NO: 5, SEQ ID NO: 6, SEQ ID NO: 7, SEQ ID NO: 8, SEQ ID NO: 9 SEQ ID NO: 10, SEQ ID NO: 11, SEQ ID NO: 12 and SEQ ID NO: 15.

In some embodiments, the method to modify, maintain, or increase tissue levels of ELOVL2 enzyme further comprises administering an additional therapeutic agent. In some embodiments, the additional therapeutic agent may be a C18-C28 polyunsaturated fatty acid. In some embodiments, the additional therapeutic agent may be an anti-inflammatory agent. In some embodiments, the additional therapeutic agent may be a steroid. In some embodiments, the steroid may be a corticosteroid. In some embodiments, the additional therapeutic agent may be a demethylating agent. In some embodiments, the demthylating agent may be decitabine. In some embodiments, the additional therapeutic agent may be decitabine-PLGA. In some embodiments, the additional therapeutic agent may be selected from bevacizumab, ranibizumab, afibercept, lucentis, eylea, beovu, brolucizumab, macugen, ranibizumab, visudyne, aflibercept, vertecporfin, pegaptanib, or a combination thereof.

In some embodiments, the method to modify, maintain, or increase tissue levels of ELOVL2 enzyme may be administered by sub-retinal injection. In some embodiments, the method to modify, maintain, or increase tissue levels of ELOVL2 enzyme may be administered by intravitreal administration. In some embodiments suprachoroidal administration may be used. In some embodiments the method to modify, maintain, or increase tissue levels of ELOVL2 enzyme may be administered by intravenous administration. In some embodiments, administration may be via a narrow gauge needle or a cannula type device for delivering the composition.

In some aspects, a method of reducing or slowing-down an aging phenotype in a subject in need thereof may be described herein. In some embodiments, the method comprises administering the subject a composition comprising an optimized polynucleotide sequence that increases the tissue levels of ELOVL2. In some cases, the aging phenotype comprises the aging phenotype comprises a decrease in photoreceptors in an eye, retinal function, oxidative stress, age-related macular degeneration, diabetic eye disease, or dry eyes. In some embodiments, the optimized polynucleotide sequence comprises a polynucleotide sequence of SEQ ID NO: 2 or a sequence exhibiting at least 95% identity to SEQ ID NO: 2. In some embodiments, the optimized polynucleotide sequence comprises a polynucleotide sequence of SEQ ID NO: 3 or a sequence exhibiting at least 95% identity to SEQ ID NO: 3. In some embodiments, the polynucleotide sequence further comprises a promoter, an enhancer, an inverted terminal repeats (ITR), polyadenylation signal, a signal sequence, or a combination thereof which can include but are not limited to SEQ ID NOs: 4, 5, 6, 7, 8, 9, 11, 12, and 15. In some embodiments, the optimized polynucleotide sequence further comprises a viral capsid or an envelope or a non-viral delivery system. In some embodiments, the viral capsid and envelope may be independently selected from adeno-associated virus-based (AAV), adenovirus-based, alphavirus-based, herpesvirus-based, retrovirus-based, lentivirus-based, or vaccinia virus-based. In some embodiments, the viral capsid can include but is not limited to SEQ ID NOs: 19, 20, 21, and 22. In some embodiments, the optimized polynucleotide sequence may be in a non-viral delivery system where it may be associated with or encapsulated in synthetic polymeric micro-particles. In some embodiments the optimized polynucleotide sequence may be in a DNA minicircle format.

In some embodiments, the aging-related disease or condition may be age-related macular degeneration (AMD). Age-related macular degeneration (also known as macular degeneration, AMD, or ARMD) is a worsening of vision that results in either a blurred vision or no vision at the center of the visual field. In some embodiments, oxidative stress, lipid molecule accumulation, and inflammation contribute to the development of AMD. In some cases, a composition comprising a vector described above treat AMD. In other cases, a composition comprising a vector described above reduces and/or slows-downs the progression of AMD. In some embodiments, the aging-related disease or condition may be cataracts. In some embodiments, the aging-related disease or condition may be glaucoma. In some embodiments, the aging-related disease or condition may be dry eye syndrome. In some embodiments, the aging-related disease or condition may be low vision.

In some embodiments, the aging-related disease or indication may be a metabolic disease or condition. In some embodiments, the age-related disease or indication may be Alzheimer's disease. In some embodiments, the age-related disease or indication may be non-alcoholic fatty liver disease. In some embodiments, the age-related disease or indication may be cancer. In some embodiments, the age-related disease or indication may be retinitis pigmentosa. In some embodiments, the age-related disease or indication may be a corneal disease. In such embodiments, the metabolic disease or condition may be diabetes (diabetes mellitus, DM). In some cases, diabetes is type 1 diabetes, type 2 diabetes, type 3 diabetes, type 4 diabetes, double diabetes, latent autoimmune diabetes (LAD), gestational diabetes, neonatal diabetes mellitus (NDM), maturity onset diabetes of the young (MODY), Wolfram syndrome, Alstrom syndrome, prediabetes, or diabetes insipidus. Type 2 diabetes, also called non-insulin dependent diabetes, is the most common type of diabetes accounting for 95% of all diabetes cases. In some cases, type 2 diabetes is caused by a combination of factors, including insulin resistance due to pancreatic beta cell dysfunction, which in turn leads to high blood glucose levels. In some cases, increased glucagon levels stimulate the liver to produce an abnormal amount of unneeded glucose, which contributes to high blood glucose levels.

In some embodiments, the optimized polynucleotide sequence may be formulated as a composition for upregulating the expression of one or more additional genes. In such embodiments, the method comprises treating a subject in need thereof, which comprises administering to the subject a composition comprising the vector comprising a polynucleotide encoding the one or more additional genes or a functionally-active fragment thereof. In some embodiments, the therapeutic agent may be formulated as a composition for upregulating the expression of ELOVL2 in combination with one or more of additional genes selected from Slc6a4, Sst, Hdac4, Nefm, Calbl, I14U, Grin2c, Chga, Grm2, Neurodl, Ardbl, Dio3, Ghsr, Avprla, Cadps2, Gria2, Irs2, Smad2, Htr7, Sypl2, Madlll, Vgf, or a combination thereof.

In some aspects, a method of treating, ameliorating or preventing an age-related eye disease or condition is described herein. In some embodiments, the method comprises administering the subject a composition comprising an optimized polynucleotide sequence that increases the tissue levels of ELOVL2. In some embodiments, the optimized polynucleotide sequence comprises a polynucleotide sequence of SEQ ID NO: 2 or a sequence exhibiting at least 95% identity to SEQ ID NO: 2. In some embodiments, the optimized polynucleotide sequence comprises a polynucleotide sequence of SEQ ID NO: 3 or a sequence exhibiting at least 95% identity to SEQ ID NO: 3. In some embodiments, the polynucleotide sequence further comprises a promoter, an enhancer, an inverted terminal repeats (ITR), polyadenylation signal, a signal sequence, or a combination thereof which can include but are not limited to SEQ ID NOs: 4, 5, 6, 7, 8, 9, 11, 12, and 15. In some embodiments, the optimized polynucleotide sequence further comprises a viral capsid or an envelope or a non-viral delivery system. In some embodiments, the viral capsid and envelope may be selected from an adeno-associated virus-based (AAV), adenovirus-based, alphavirus-based, herpesvirus-based, retrovirus-based, lentivirus-based, or vaccinia virus-based. In some embodiments the viral capsid can include but are not limited to SEQ ID NOs: 19, 20, 21, and 22. In some embodiments, the optimized polynucleotide sequence may be in a non-viral delivery system where it may be associated with or encapsulated in synthetic polymeric micro-particles. In some embodiments the optimized polynucleotide sequence may be in a DNA minicircle format. In some embodiments, the composition may be administered systemically using and an intravenous route. In some embodiments localized administration is utilized. For ocular administration an intravitreal, subretinal, subconjunctival, subtenon, or posterior juxtascleral route may be utilized. In some embodiments, the age-related eye disease may be age-related macular degeneration (AMD), diabetic eye disease, glaucoma, low vision or dry eye.

Therapeutic Regimens

The present disclosure, provides pharmaceutical formulations, and kits for use in the treatment of a subject. In some embodiments, the subject is a mammal. In some embodiments, the subject is a human. In some embodiments, the formulations provide a therapeutic benefit to a subject in need of treatment for an eye disease.

In some aspects, a formulation as described herein is provided to a subject to treat, prevent, or ameliorate a disease or condition associated with vision loss. In some embodiments, the vision loss may be caused by a retinal disorder. In some embodiments, the retinal disorder may be age-related macular degeneration. In some embodiments, the formulation further comprises a pharmaceutically acceptable aqueous or non-aqueous medium. In some embodiments, the administration may be a sub-retinal injection.

In some aspects, the formulation as described herein results in increased levels of ELOVL2 enzyme in in the eye of a subject. In some embodiments, the formulation further comprises a pharmaceutically acceptable aqueous or non-aqueous medium. In some embodiments, the administration may be a sub-retinal injection. In some embodiments, the formulation may be administered in a volume from about 10 μl to about 200 μL. In some embodiments, the volume is about 50 μL. In some embodiments, the compositions as described herein are administered subretinally to an eye. In some embodiments, a single administration of the compositions as described herein is sufficient for therapeutic treatment. In some embodiments repeat administrations are required for therapeutic treatment. While not intended to be limiting, in some embodiments the therapeutic agent described herein is administered at intervals of 3 months, six months, 12 months, 18, months, 24 months, 30 months, 36 months 42 months, 48 months, 54 months, 60 months, 66 months, 72 months or combinations thereof. In some embodiments, the composition is described herein is administered after administration of a corticosteroid. In some embodiments, a corticosteroid is administered to a subject, followed by administration of a composition as described herein, followed by administration of a corticosteroid.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Treatments exhibiting high therapeutic indices are preferred. The data obtained from cell culture assays and animal studies are used in formulating a range of dosage for use in human. The dosage varies within this range depending upon the dosage form employed and the route of administration utilized.

EXAMPLES

The following examples are intended to illustrate details of the disclosure, without thereby limiting it in any manner.

Example 1

The ELOVL2 wild type sequence was obtained using the University of California Santa Cruz (UCSC) genome browser (RefSeq_NM017770). A series of codon optimized variants were generated using codon optimization. ELOVL2 codon variants were aligned using the MUSCLE (www.ebi-.ac.uk/Tools/msa/muscle/) multiple alignment program and only sequences that were significantly different from one another were accepted. ELOVL2 wild type (WT), and a set of five codon variants were cloned into the plasmid pAAV-EF1a.

The plasmid pAAV-EF1a, contains the human EF1a promoter, optimized Kozak, P2A sequence linking ELOVL2 to a GFP reporter, a wpre element, and the human growth hormone polyA tail. The plasmid pAAV-CMV contains the human cytomegalovirus promoter, optimized Kozak, P2A sequence linking ELOVL2 to a GFP reporter, a wpre element, and the human growth hormone polyA tail. The plasmid pAAV-CMVT contains the human cytomegalovirus promoter, adenovirus tripartite leader, optimized Kozak, P2A sequence linking ELOVL2 to a GFP reporter, a wpre element, and the human growth hormone polyA tail. The plasmid pAAV-CMVT-HR contains a human ELOVL2 enhancer element, human cytomegalovirus promoter, adenovirus tripartite leader, optimized Kozak, P2A sequence linking ELOVL2 to a GFP reporter, a wpre element, and the human growth hormone polyA tail. The minicircle CMVT-CV4-GFP contains the human cytomegalovirus promoter, adenovirus tripartite leader, optimized Kozak, P2A sequence linking ELOVL2 to a GFP reporter, a wpre element, and the human growth hormone polyA tail with very little of the bacterial plasmid backbone. The AAV vector AAV8-CMVT-CV4-GFP contains the AAV2 ITRs, human cytomegalovirus promoter, adenovirus tripartite leader, optimized Kozak, P2A sequence linking ELOVL2 to a GFP reporter, a wpre element, and the human growth hormone polyA tail in an AAV8 capsid.

Retinal pigmented epithelial cells (ARPE19 from the ATCC), were plated at $3\times10^5$ cells per well into a 6-well plate. The following day, each well was transfected using 2.5 μg of each plasmid (ELOVL2 WT and codon variants) and Lipofectamine 3000 in 250 μl total volume by a drop wise manner. The media was changed after an eight-hour incubation at 37° C. and 5% $CO_2$. The cells were then allowed to rest for an additional 48 hours at 37° C. and 5% $CO_2$. Forty-eight hours post transfection, cells were trypsinized, washed in 1×PBS, fixed for 30 min and resuspended in flow 500 μl buffer. The following day the cells were analyzed by flow cytometry on an LSRII instrument (BD Biosciences). GFP expression percentage and mean fluorescent intensity (MFI) were measured and used to determine relative expression levels.

Example 2

In this experiment, ARPE19 cells were transfected with ELOVL2 expression constructs, wild type, codon variant 1 (CV1) as a minicircle and plasmid, and codon variant 4 (CV4) as shown in FIG. 1. These constructs all used the human EF1a promoter to drive expression. It was observed that changing codons to optimize for expression in the retina was able to show different levels of in vitro expression. The CV1 (SEQ ID NO: 2) variant in a minicircle expressed at 1.61× that of wild type. The CV1 plasmid expressed at 1.33× that of wild type. The CV4 (SEQ ID NO: 3) variant in a plasmid expressed at 1.82× that of wild type. This experiment demonstrated that the codon optimization led to better expression over the wild-type.

Figure 2:
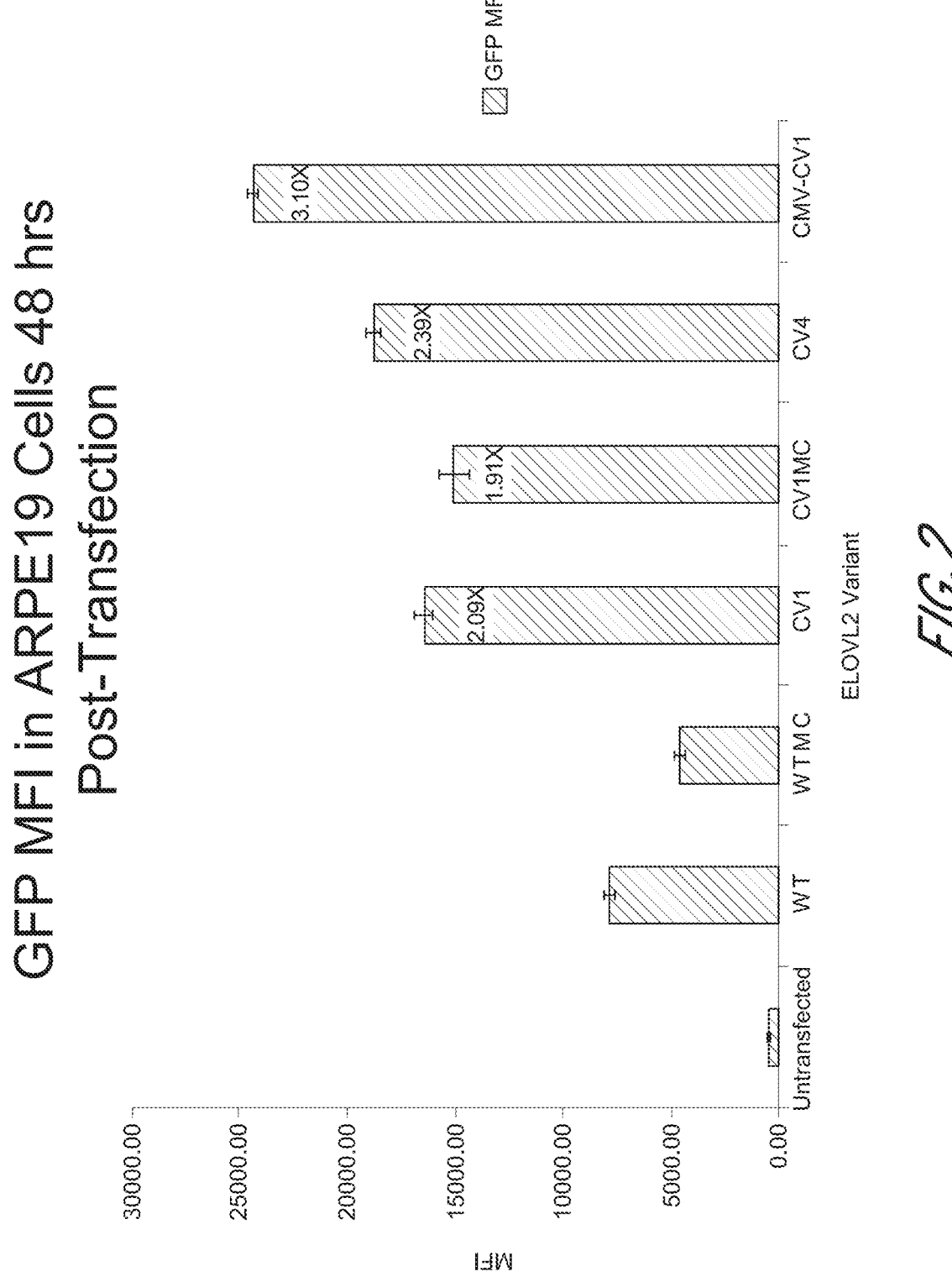
FIG. 2 is a bar graph that illustrates expression of ELOVL2/GFP protein 48 hours after transfection in ARPE19 cells transfected with ELOVL2/GFP expression constructs using the EF1a promoter compared to the CMV promoter (CMV-CV1).

FIG. 2 shows the results of another experiment wherein ARPE19 cells transfected with ELOVL2 expression constructs using the EF1a promoter were compared to constructs using the CMV promoter. This experiment demonstrated that at 48 hours after transfection constructs having the CMV promotor had an increased expression. Specifically, EF1a-CV1 expressed at 2.09× that of wild type, EF1a-CV4 expressed at 2.39× that of wild type and CMV-CV1 expressed at 3.10× that of wild type.

Figure 3:
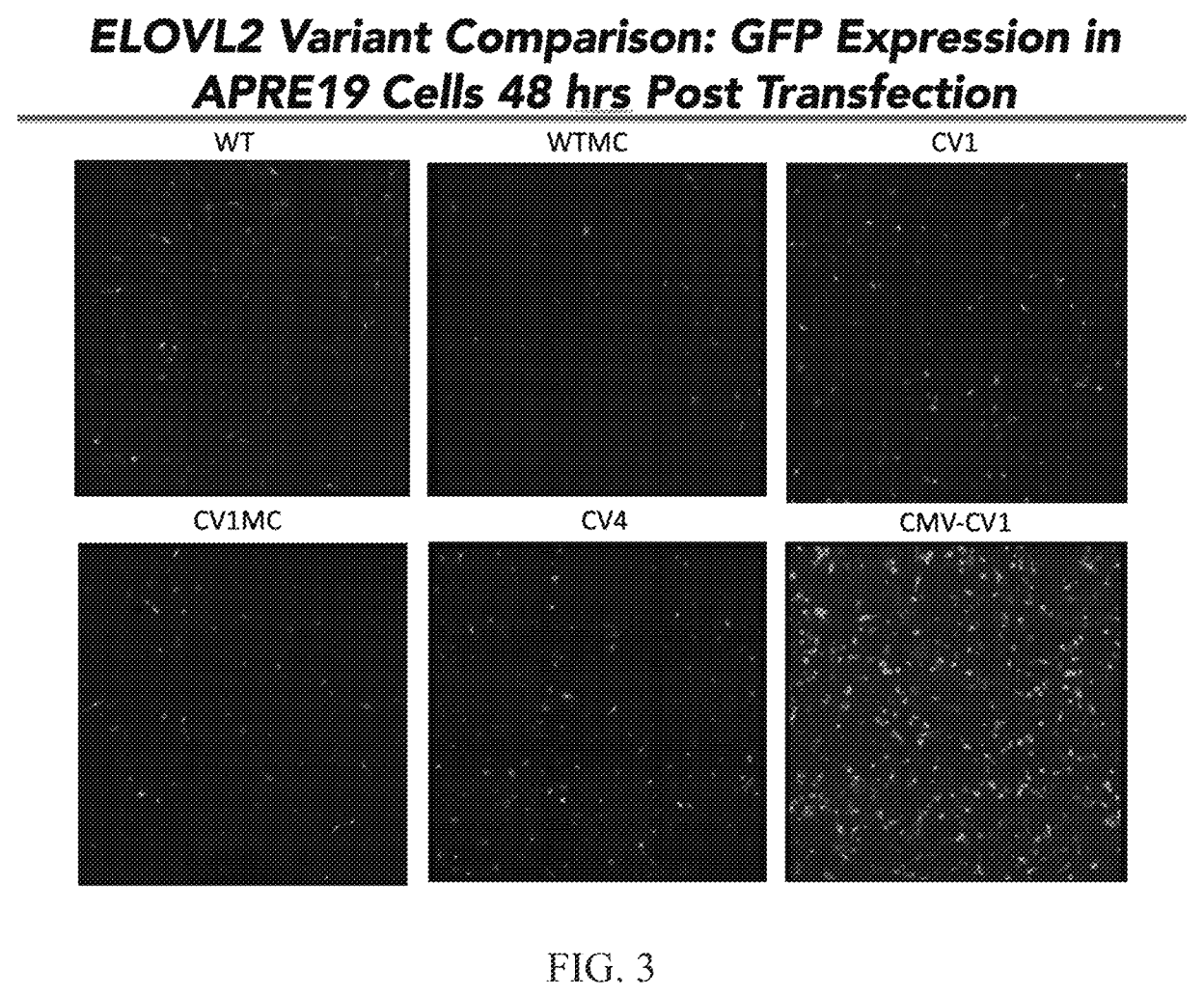

FIG. 3 shows a set of microscope images of the GFP expression found in ARPE19 cells transfected with the ELOVL2 expression constructs mentioned above. The GFP expression is highest in the CMV-CV1 construct compared to those using the EF1a promoter. As shown in FIG. 3, it is visibly detectable that the cells expressing the CMV promotor constructs give much higher expression. This is further evidenced in a ELOVL2 Western Blot as shown in FIG. 4.

Figure 4:
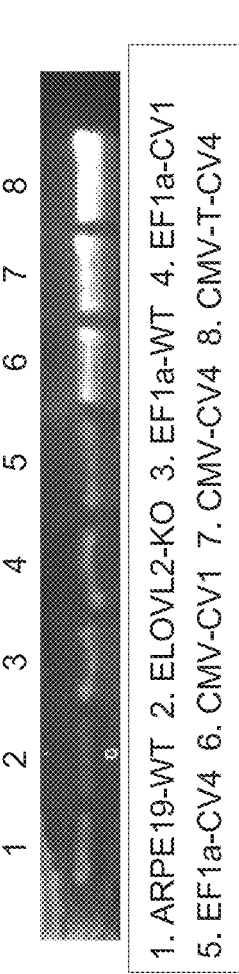
FIG. 4 is a western blot that illustrates ARPE19 cells transfected with ELOVL2 expression constructs. The expression constructs include ELOVL2 wild type (ARPE19-WT), ELOVL2 knock-out (ELOVL2-KO), ELOVL2 wild type of EF1a promoter (EF1a-WT), ELOVL2 codon variant 1 (SEQ ID NO: 2) attached to the EF1a promoter (EF1a-CV1), ELOVL2 codon variant 4 (SEQ ID NO: 3) attached to the EF1a promoter (EF1a-CV4), ELOVL2 codon variant 1 (SEQ ID NO: 2) attached to the CMV promoter (CMV-CV1), ELOVL2 codon variant 4 (SEQ ID NO: 3) attached to the CMV promoter (CMV-CV4), and ELOVL2 codon variant 4 (SEQ ID NO: 3) attached to the CMV promoter (CMVT-CV4) and ELOVL2 codon variant 4 (SEQ ID NO: 3) attached to the CMV promoter with a tripartite leader.

FIG. 4 is a western blot that illustrates ARPE19 cells transfected with ELOVL2 expression constructs. The expression constructs include ELOVL2 wild type (ARPE19-WT), ELOVL2 knock-out (ELOVL2-KO), ELOVL2 wild type of EF1a promoter (EF1a-WT), ELOVL2 codon variant 1 (SEQ ID NO: 2) attached to the EF1a promoter (EF1a-CV1), ELOVL2 codon variant 4 (SEQ ID NO: 3) attached to the EF1a promoter (EF1a-CV4), ELOVL2 codon variant 1 (SEQ ID NO: 2) attached to the CMV promoter (CMV-CV1), ELOVL2 codon variant 4 (SEQ ID NO: 3) attached to the CMV promoter (CMV-CV4), and ELOVL2 codon variant 4 (SEQ ID NO: 3) attached to the CMV promoter with a tripartite leader (CMV-T-CV4). As shown, the expression of the CMV constructs was higher than with the EF1a promotor. Of the CMV constructs, lane 8, corresponding to the ELOVL2 codon variant 4 attached to the CMV promoter with a tripartite leader (CMV-T-CV4) appeared to have the highest expression.

Figure 5:
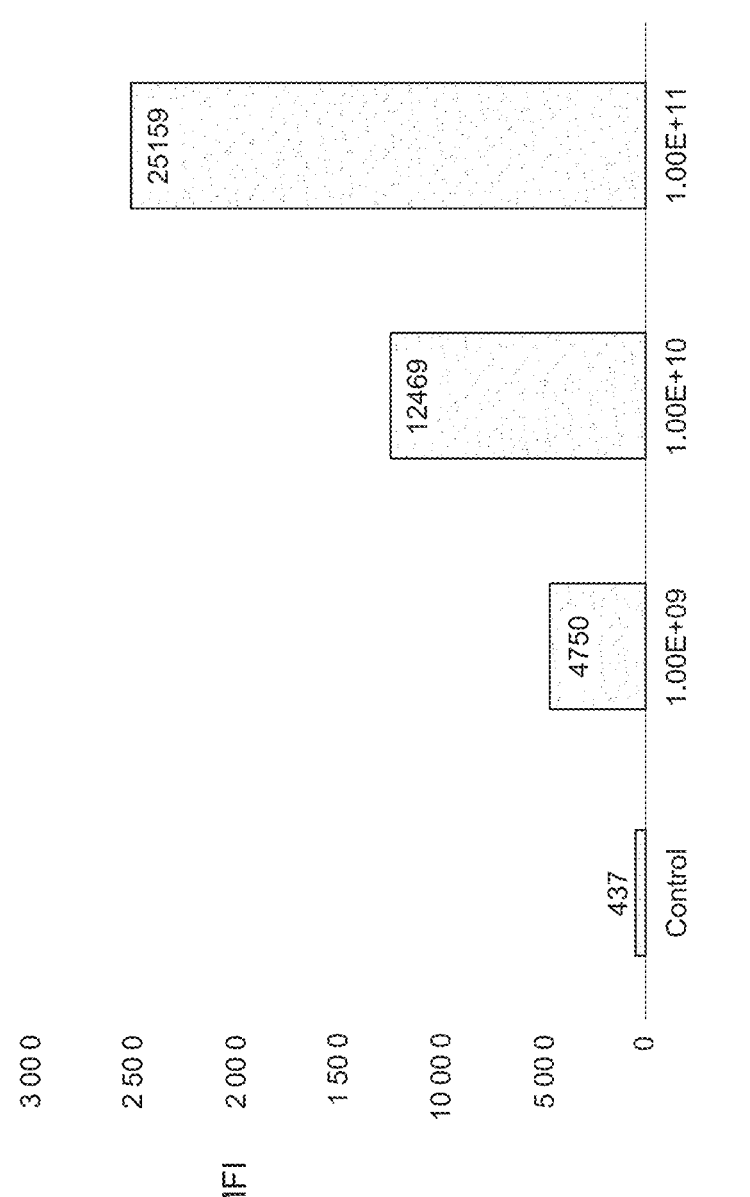
FIG. 5 is a bar graph that illustrates a dose response of ELOVL2 expression in ARPE19 cells transduced with AAV8-CMVT-CV4 vectors. The cells were transduced with $1 \times 10^9$, $1 \times 10^{10}$, or $1 \times 10^{11}$ viral genomes.

FIG. 5 is a bar graph that illustrates a dose response of ELOVL2 expression in ARPE19 cells transduced with AAV8-CMVT-CV4 vectors. The cells were transduced with $1\times10^9$, $1\times10^{10}$, or $1\times10^{11}$ viral genomes. As shown, the dose of $1\times10^9$ led to 4750 MFI. The dose of $1\times10^{10}$ led to 12469 MFI and the dose of 1×1011 led to 25159 MFI.

Figure 6:
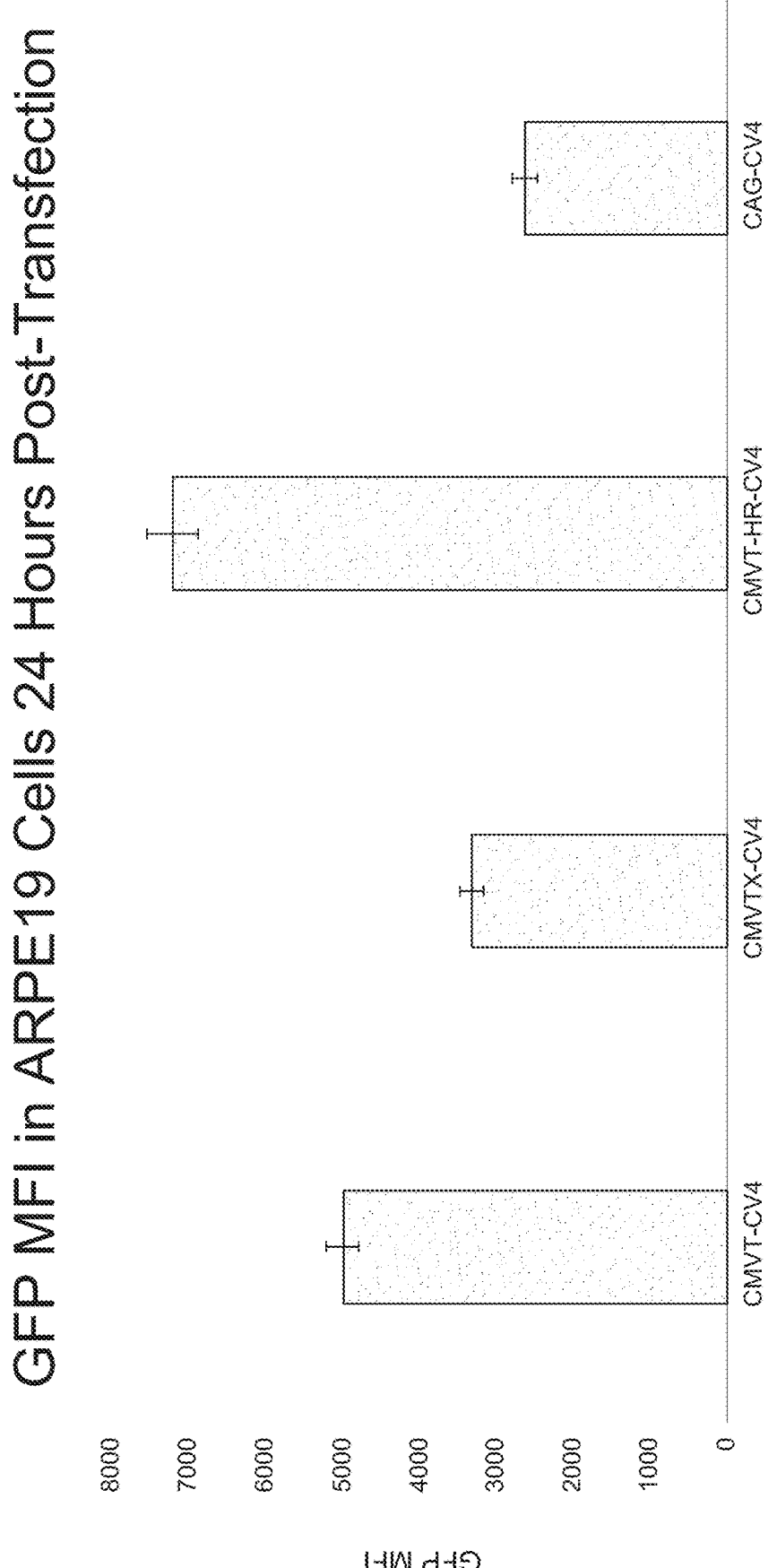
FIG. 6 is a bar graph that illustrates the expression of ELOVL2 protein in ARPE19 cells transfected with ELOVL2 expression constructs. The first expression construct was with the addition of the adenovirus tripartite leader sequence (CMVT-CV4). The second construct was the addition of a human factor IX intron (CMVTX-CV4), the third construct was with both the adenovirus tripartite leader sequence and a human ELOVL2 enhancer sequence (CMVT-HR-CV4) and the fourth construct was the CMV enhancer, chicken beta-Actin promoter and a rabbit beta-Globin mini intron (CAG-CV4).

FIG. 6 is a bar graph that illustrates the expression of ELOVL2 protein in ARPE19 cells transfected with ELOVL2 expression constructs. The first expression construct was with the addition of the adenovirus tripartite leader sequence (CMVT-CV4). The second construct was the addition of a human factor IX intron (CMVTX-CV4), the third construct was with both the adenovirus tripartite leader sequence and a human ELOVL2 enhancer sequence (CMVT-HR-CV4) and the fourth construct was the CMV enhancer, chicken beta-Actin promoter and a rabbit beta-Globin mini intron (CAG-CV4).

Figure 7:
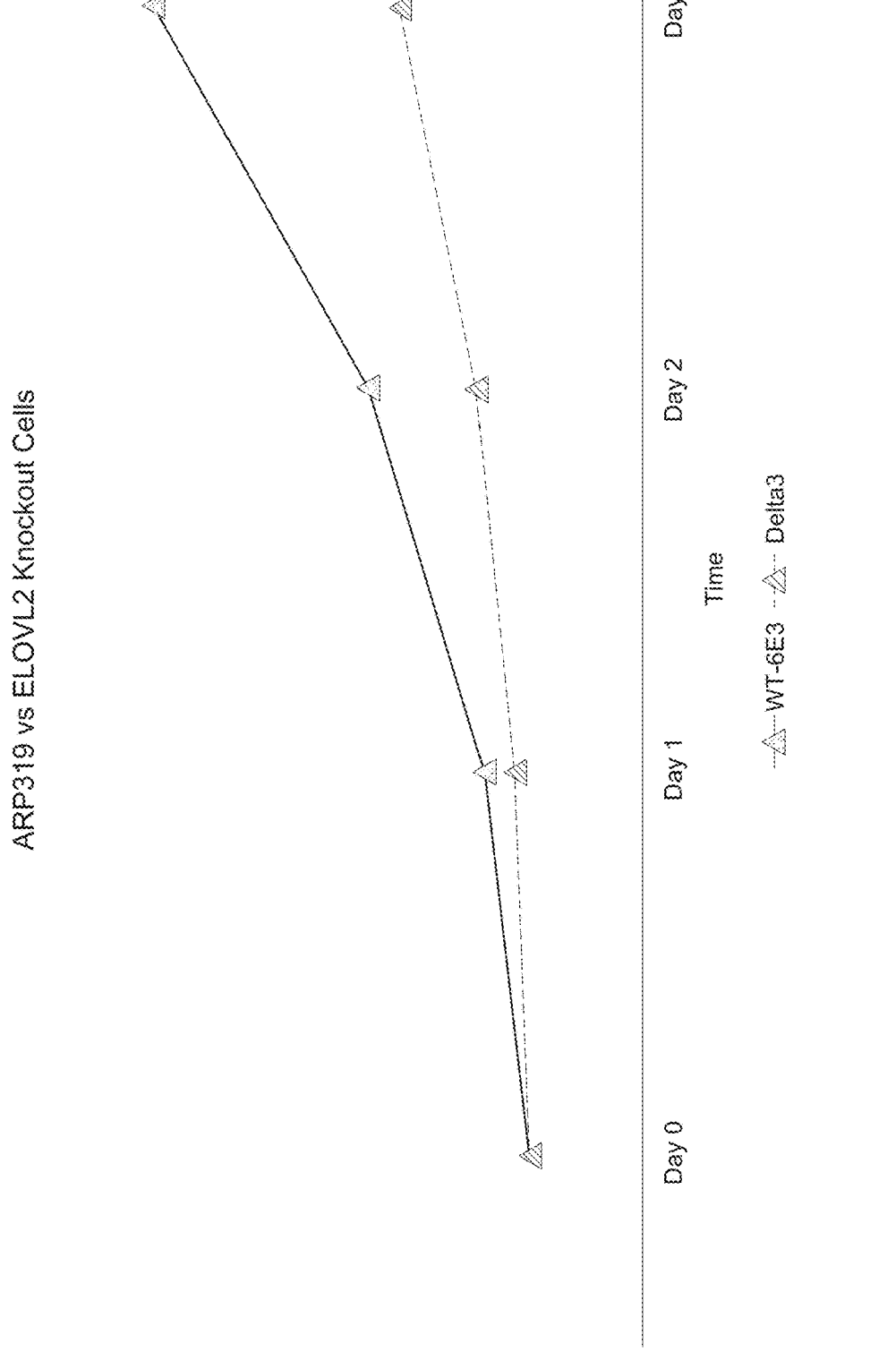
FIG. 7 is a line chart that illustrates the ELOVL2 knock-out cell line (Delta3) has a significant growth defect when compare to the wild type ARPE19 cells (WT-6E3).

FIG. 7 is a line chart that illustrates the ELOVL2 knock-out cell line (Delta3) has a significant growth defect when compare to the wild type ARPE19 cells (WT-6E3). At day 3, the WT-6E3 cells were growing at a relative growth rate of 4.2, in comparison to the Delta3 knockout cell line with a growth rate of 2.

Example 3

In this Example, the AAV and minicircle vectors expressing ELOVL2/GFP were administered as subretinal injections. C57BL/6JRj male mice aged 12 months at treatment administration (Janvier, France) were housed in individually ventilated cages with aspen bedding, nesting material (Populus tremula, Tapvei® Estonia OÜ, Estonia) and polycarbonate igloos (Datesand group, USA) as enrichment, at a constant temperature (22±1° C.), relative humidity (50±10%) and in a light-controlled environment (lights on from 7 am to 7 pm) with ad libitum access to food (Rat/Mouse maintenance V1535-000, ssniff Spezialdiäten GmbH, Germany) and tap water. Experiments were started after a minimum of one-week quarantine and acclimatization in the vivarium.

All animals were treated in accordance with the ARVO Statement for the Use of Animals in Ophthalmic and Vision Research the EC Directive 2010/63/EU of the European Parliament and of the Council on the Protection of animals used for Scientific Purposes and using protocols approved and monitored by the Animal Experiment Board of Finland (Experimentica Ltd. animal license number ESAVI-10750-2020).

For all the procedures the animals were anesthetized with a s.c. injection of a mixture containing ketamine (30 mg/Kg) (Ketaminol Vet 50 mg/mL. Intervet, Germany) and medetomidine (0.4 mg/kg) (Cepetor Vet 1 mg/mL. Vetmedic, Finland). Anesthesia was reversed by α2-antagonist for medetomidine (2.5 mg/kg) (Revertor Vet 5 mg/mL; Vetmedic).

Figure 8:
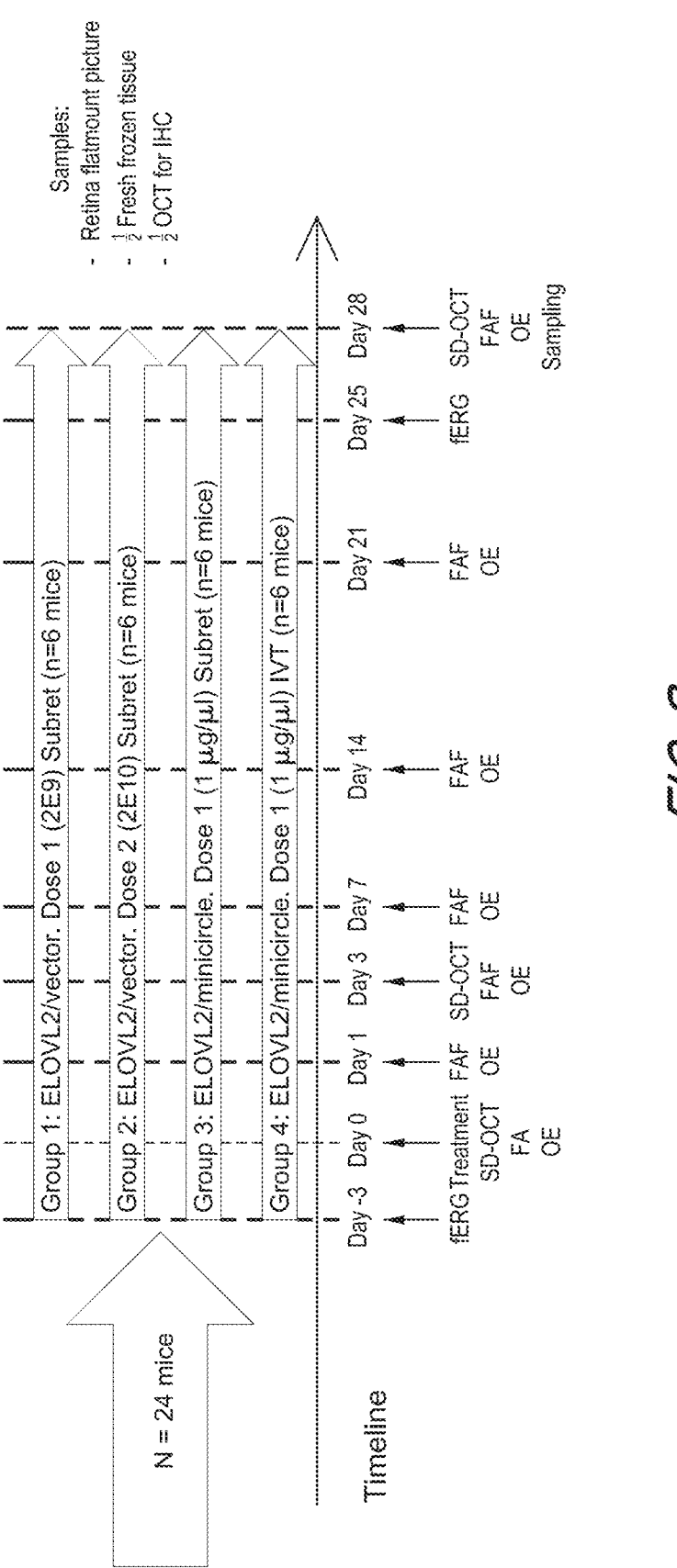
FIG. 8. is a schematic chart showing the administration schedule of four groups of mice injected with AAV or minicircle vectors expressing ELOVL2/GFP vectors according to one embodiment.

As shown in FIG. 8, Groups 1 and 2 were dosed with AAV/ELOVL2/GFP constructs as subretinal injections while groups 3 and 4 were dosed with minicircle/ELOVL2/GFP constructs as subretinal and intravitreal injections, respectively. For each group, half of the animals in the group were administered bilaterally the test vector, while the other half received the test vector in the OD eye and the OS eye was treated with a control vector having GFP.

To perform the injections, the anesthetized animals were placed under a stereoscope (Leica Microsystems), and a drop of iodine was applied on the cornea and allowed to spread evenly (Minims Povidione Iodine 5%, Bausch & Lomb, Canada). A small incision with a 30 G needle was performed in the temporal side of the conjunctiva/sclera in order to expose the choroid. The same needle was used to create a small opening in the temporal side of the choroid. The cornea was punctured in order to reduce the intraocular pressure. A microsyringe (Hamilton Bonaduz AG, Bonaduz, Switzerland) was filled with 1 μl solution of AAV/Minicircle and the viral vector was introduced into the subretinal space through the exposed choroid.

The solution was injected into the subretinal space for 10 sec. The needle was kept in place for additional 30 seconds before being removed. Successful injections were confirmed using in vivo SD-OCT imaging (Bioptigen Envisu R2210. Bioptigen Inc./Leica Microsystems, Morrisville, NC, USA). Chloramphenicol ointment was applied after the injection (Oftan Chlora, Santen Oy, Finland). For each treatment group, half of the animals were administered bilaterally the test vector, while the other half received the test compound in the OD eye and the OS were treated with a control GFP vector as shown in FIG. 8.

The eyes were monitored using OE, FAF on days 0, 1, 3, 7, 14, 21 and 28, and with SD-OCT on days 0, 3 and 28.

Macroscopic ophthalmic examination were performed on anesthetized mice as described above, and they received a drop of 0.5% tropicamid (Oftan Tropicamid, Santen Oy, Finland), to dilate the pupils. The mice were placed on a slit lamp (SL9900 Elite 5X-D. CSO srl, Italy), and both eyes of the animals examined.

Transduction of the retina by GFP AAV/Minicircle-vectors were examined using a Heidelberg Spectralis HRA2 system (Heidelberg Engineering, Germany). Briefly, a drop of 0.5% tropicamid (Oftan Tropicamid. Santen Oy) were administered on the cornea of the anesthetized mouse, in order to dilate the pupils, and the mouse was placed onto the mouse holder. After aligning the optic nerve head at the retina level, with the use of the infrared reflectance camera, a fluorescence image will be taken showing all the transduced area at the retina level.

Mice were killed by anesthesia overdose, and were transcardially perfused with 0.9% NaCl solution (120S/DV manual Control Variable Speed Pump. Watson-Marlow Pumps, UK). The eyes were enucleated and retinal flat-mounts prepared.

The freshly excised whole eye flat-mounts were imaged using a fluorescent microscope (MST69. Leica Microsystems, Germany).

Figure 9:
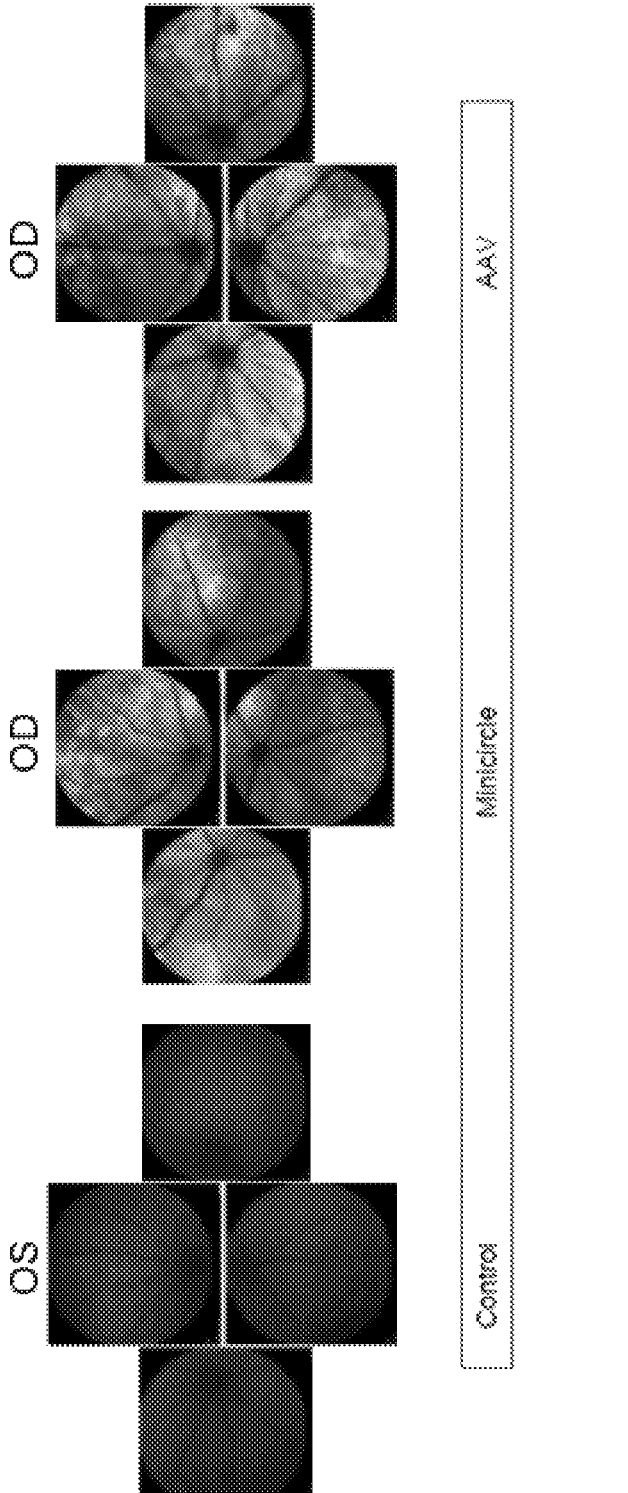
FIG. 9 is an image that illustrates AAV8-CMVT-CV4-GFP (dose: 2E10 vg/eye, sub retinal), MiniCircle CMVT-CV4-GFP (dose: 2 μl of 1 μg/μl, intravitreal) and injection control were administered to aged 12 month old C57BL/6JRj mice. Fundus autoflourescense imaging using a Heidelberg Spectralis HRA2 system (Heidelberg Engineering, Germany) on day 14 post administration shows significant fluorescence in the treated mice vs the mice receiving control injections. The fluorescence intensity was found to be directly proportional to GPF/ELOVL2 gene expression.

Representative results of this study can be seen in FIG. 9 which show little or no fluorescence in control animals (PBS) compared to a high degree of fluorescence in mice dosed with AAV or minicircle vectors comprising the ELOVL2 gene linked to GFP. Since the GFP and ELOVL2 gene transcription were directly linked in the minicircle and AAV vectors, the fluorescence resulting from expression of GFP is a direct surrogate of ELOVL2 expression.

Example 4

In this Example, the efficacy of an AAV vector expressing the ELOVL2 protein (AAV8-HRCMVT-CV4) gene therapy in aging mice who exhibit diminishing ocular activity with age as a model for macular degeneration was investigated. In this study, AAV8-HRCMVT-CV4 vector in a buffer was administered as a single subretinal injection to the right eye of 12-month old C57BL/6JRj mice (Janvier, France) at either a low, mid, or high dose as follows: Low dose $(5\times10E^7$ vg/eye), Mid dose $(2\times10E^8$ vg/eye), and High dose $(8\times10E^8$ vg/eye). In addition, the left eye of each mouse was treated with vehicle as a control. At two weeks and 12 weeks post-administration, spectral domain optical coherence tomography SD-OCT was performed to assess retinal structure (degeneration) together with flash electroretinography (fERG) to assess retinal function.

For this study, C57BL/6JRj male mice aged 12 months at treatment administration were housed in individually ventilated cages with aspen bedding, nesting material and polycarbonate igloos at a constant temperature ($22\pm1°$ C.), relative humidity ($50\pm10\%$) and in a light-controlled environment (lights on from 7 am to 7 pm) with ad libitum access to food and tap water. The experiment started after a minimum of one-week quarantine and acclimatization in the vivarium.

Anesthetized animals were placed under a stereoscope, and a drop of iodine was applied on the cornea and allowed to spread evenly. A small incision with a 30 G needle was made in the temporal side of the conjunctiva/sclera in order to expose the choroid. The same needle was used to create a small opening in the temporal side of the choroid. The cornea was punctured in order to reduce intraocular pressure.

A microsyringe filled with 1 μl of either PBS or PBS containing AAV8-HRCVMT-CV4 and was introduced into the subretinal space through the exposed choroid. Treatments were injected into the subretinal space over 10 seconds, and the needle was kept in place for additional 30 seconds before being removed. The success of the injections was confirmed using in vivo SD-OCT imaging. Chloramphenicol ointment was applied after the injection. AAV8-HRCMVT-CV4 in phosphate buffered saline (PBS) was administered in the right eye (OD), while the left eye (OS) was injected with PBS (vehicle) only.

Spectral Domain Optical Coherence Tomography (SD-OCT). Anesthetized mice were assessed via retinal scan using the Envisu R2200 SD-OCT system (Bioptigen Inc./Leica Microsystems). The scanned area covered a 1.4×1.4 $mm^2$ of the retina centered around the optic nerve. Each scan was composed of 100 B Scans each composed of 1000 A Scans.

Flash Electroreinography (fERG). Retinal function was quantified bilaterally using flash electroretinography (fERG). For scotopic fERG measurements, animals were dark-adapted over-night. All preparations for ERG were performed under dim red light. Mice were anesthetized as described above and secured on the heating pad surface of the Celeris ERG system (Diagnosys LLC). Pupils were fully dilated by applying a drop of 0.5% tropicamide (Oftan Tropicamid. Santen Oy) for 3 min, followed by a drop of 10% phenylephrine hydrochloride (Oftan Metaoksedrin. Santen Oy) for an additional 3 min. During fERG recordings, eyes were lubricated using physiological saline. Lubrication with saline also ensured the electrical contact between the cornea and the light guide electrode.

fERG was tested at a light intensity of 1.0 cd·s/m². Responses were recorded six consecutive times and averaged and used to identify the amplitudes (in µV) and latencies (in ms) for both a- and b-waves.

Figures 10A, 10B:
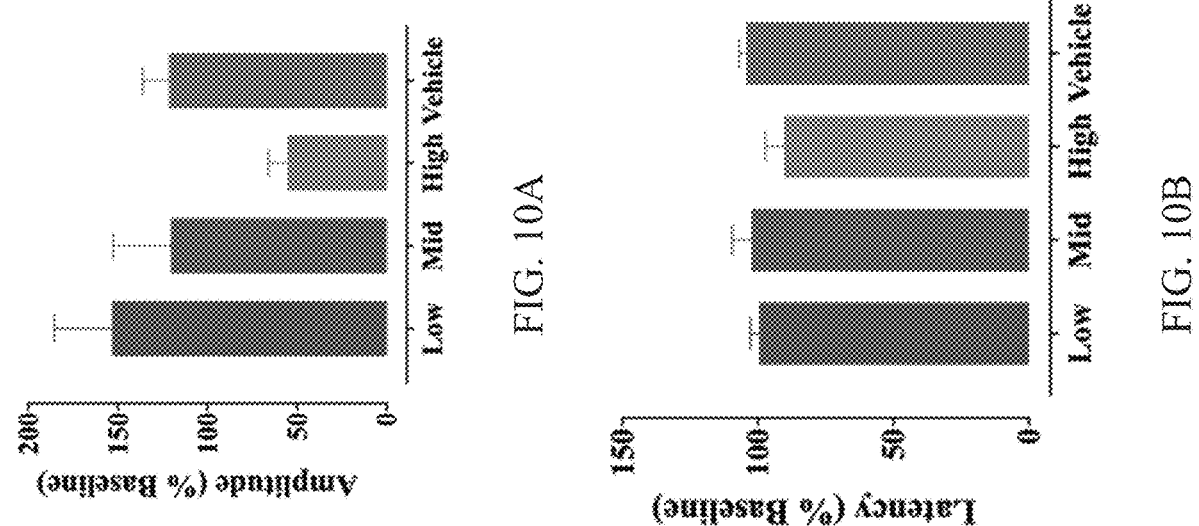
FIG. 10A is a bar graph that illustrates retinal function analyzed by fERG at cd·s/m² luminance a-wave amplitude relative to the baseline levels.
FIG. 10B is a bar graph that illustrates retinal function analyzed by fERG at cd·s/m² luminance a-wave latency relative to the baseline levels.

FIG. 10A illustrates the amplitude of the 12 week fERG a-wave and FIG. 10B a-wave latency period as a percentage of the week 2 response for the various treatment groups. Compared to the vehicle, there was a decrease in the amplitude of the a-wave for both the high and mid-dose groups. In contrast, the low dose AAV8-HRCMVT-CV4 maintained a greater amplitude of fERG a-wave compared to the other treatment groups (including vehicle). There was no meaningful change in the a-wave latency among the treatment arms. Since the a-wave of a fERG reflects the function of the photoreceptors, these results suggest treatment with low dose AAV8-HRCMVT-CV4 expressing ELOVL2 improved photoreceptor function. FIG. 10A and FIG. 10B data are presented as change from baseline as a mean±SEM from 11 eyes from the Mid dose, 12 mice from the High dose, 14 mice from the Low dose, and 37 eyes from the Vehicle group.

Figures 11A, 11B:
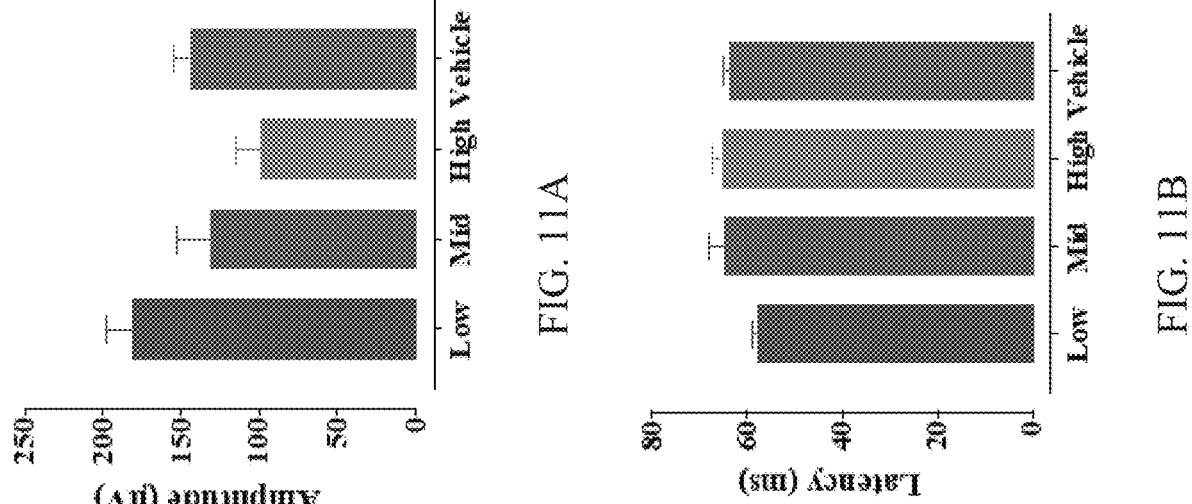
FIG. 11A is a bar graph that illustrates retinal function analyzed by fERG at cd·s/m² luminance b-wave amplitude relative to the baseline levels.
FIG. 11B is a bar graph that illustrates retinal function analyzed by fERG at cd·s/m² luminance b-wave latency relative to the baseline levels.

FIG. 11A illustrates the amplitude of the 12 week fERG b-wave and FIG. 11B illustrates the b-wave latency as a percentage of the week 2 response. Similar to the response observed for the a wave, the amplitude of the b wave was reduced compared to vehicle for both the high and mid dose groups. However, similar to that observed for the a-wave, the amplitude of the b-wave was increased for the low dose group relative to vehicle. In addition, latency of b wave response was also shortened (improved) for the low dose group (panel B). The shorter latency and increased amplitude of response demonstrates that low dose AAV8-HRCMVT-CV4 improves retinal function. FIG. 11A and FIG. 11B data are presented as absolute values as a mean±SEM from 11 eyes from the Mid dose, 12 mice from the High dose, 14 mice from the Low dose, and 37 eyes from the Vehicle group.

Figure 12:
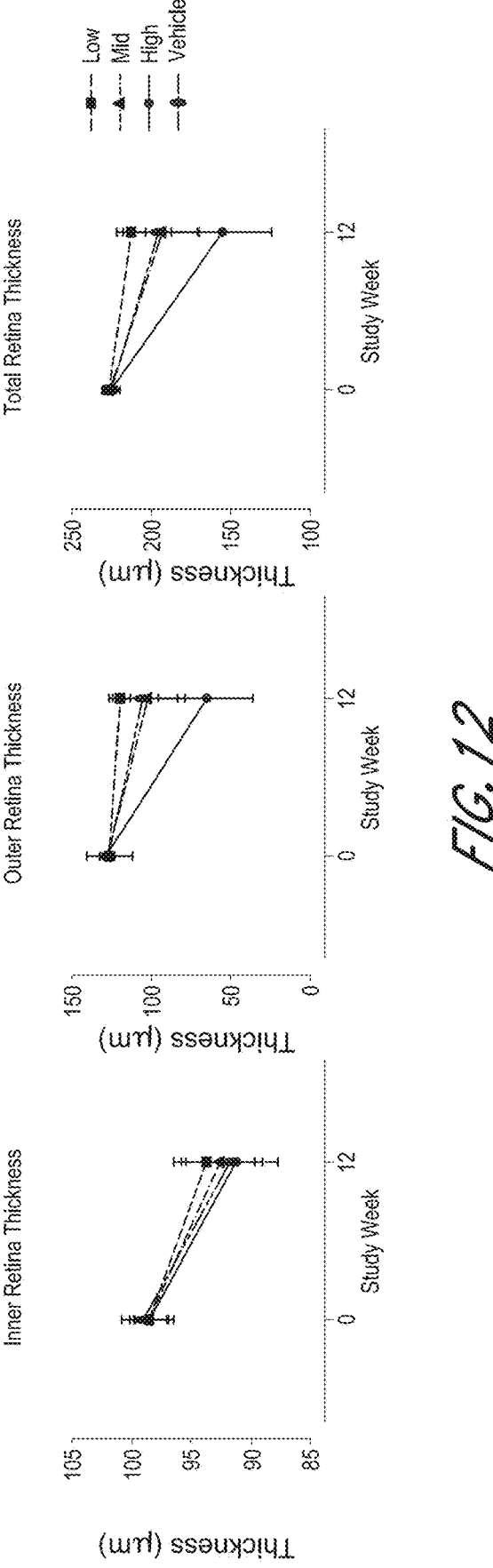
FIG. 12 is a line chart that illustrates retinal thickness for the A) inner, B) outer, and C) total retina.

FIG. 12 illustrates the change in thickness of the inner (panel A) and outer (panel B) retinal layers along with the total thickness (panel C) for the various treatment groups over the 12 week study period as measured by SD-OCT. Thinning of both the inner and outer retinal layers and total retina was observed for all treatment groups, presumably due to aging-related cell loss. However, the least amount of thinning for both the inner and outer layers and total retina was observed in the low-dose treatment group. SD-OCT is well suited for assessing retinal structure and disease related degeneration. These data demonstrate that treatment with low dose AAV8-HRCMVT-CV4 protected against age-related loss of retinal tissue. FIG. 12 data are presented as mean±SD from 11 eyes from the Mid dose, 12 mice from the High dose, 14 mice from the Low dose, and 37 eyes from the Vehicle group.

SEQUENCE LISTING

```
SEQ ID NO: 1: ELOVL2 wild-type (RefSeq_NM017770)
ATGGAACATCTAAAGGCCTTTGATGATGAAATCAATGCTTTTTTGGACAATATGT
TTGGACCGCGAGATTCTCGAGTCAGAGGGTGGTTCATGTTGGACTCTTACCTTCC
TACCTTTTTTCTTACTGTCATGTATCTGCTCTCAATATGGCTGGGTAACAAGTATA
TGAAGAACAGACCTGCTCTTTCTCTCAGGGGTATCCTCACCTTGTATAATCTTGG
AATCACACTTCTCTCCGCGTACATGCTGGCAGAGCTCATTCTCTCCACTTGGGAA
GGAGGCTACAACTTACAGTGTCAAGATCTTACCAGCGCAGGGGAAGCTGACATC
CGGGTAGCCAAGGTGCTTTGGTGGTACTATTTCTCCAAATCAGTAGAGTTCCTGG
ACACAATTTTCTTCGTTTTGCGGAAAAAAACGAGTCAGATTACTTTTCTTCATGT
ATATCATCATGCTTCTATGTTTAACATCTGGTGGTGTGTCTTGAACTGGATACCTT
GTGGACAAAGTTTCTTTGGACCAACACTGAACAGTTTTATCCACATTCTTATGTA
CTCCTACTATGGACTTTCTGTGTTTCCATCTATGCACAAGTATCTTTGGTGGAAGA
AATATCTCACACAGGCTCAGCTGGTGCAGTTCGTGCTCACCATCACGCACACCAT
GAGCGCCGTCGTGAAACCGTGTGGCTTCCCCTTCGGTTGTCTCATCTTCCAGTCA
TCTTATATGCTAACGTTAGTCATCCTCTTCTTAAATTTTTACGTTCAGACATACCG
AAAAAAGCCAATGAAGAAAGATATGCAAGAGCCACCTGCAGGGAAAGAAGTGA
AGAATGGTTTTTCCAAAGCCTACTTCACTGCAGCAAATGGAGTGATGAACAAGA
AAGCACAA SEQ ID NO: 2: Codon Variant 1 (CV1)
ATGGAACACCTGAAGGCCTTCGACGACGAGATCAACGCCTTTCTGGACAACATG
TTCGGCCCCAGAGATTCTAGAGTGCGGGGCTGGTTCATGCTGGATAGCTACCTGC
CTACATTCTTCCTGACCGTGATGTACCTGCTGAGCATCTGGCTGGGCAACAAGTA
CATGAAAAACAGACCTGCCCTGAGCCTGAGAGGCATCCTGACCCTGTACAACCT
GGGAATTACACTGCTGAGCGCCTACATGCTGGCCGAGCTGATCCTGTCAACATG
GGAGGGCGGCTACAACCTGCAGTGCCAGGACCTGACCTCCGCCGGCGAGGCCGA
CATCAGAGTGGCCAAGGTGCTGTGGTGGTACTACTTCAGCAAAAGCGTGGAATT
CCTGGACACCATCTTCTTCGTGCTGCGGAAGAAGACCAGCCAGATCACCTTCCTG
CACGTGTACCACCACGCCAGCATGTTCAACATCTGGTGGTGCGTGCTGAATTGGA
TCCCCTGCGGCCAGTCTTTTTTTGGACCTACCCTTAATAGCTTCATCCACATCCTG
ATGTACTCTTATTACGGCCTGTCTGTTTTCCCATCTATGCACAAGTACCTGTGGTG
GAAGAAATACCTGACACAGGCCCAGCTGGTCCAGTTCGTGCTCACAATCACCCA
CACCATGAGCGCCGTGGTGAAGCCTTGTGGCTTTCCATTCGGTTGTCTGATCTTTC
AGAGCAGCTACATGCTGACACTGGTGATCCTGTTCCTGAACTTCTACGTGCAGAC
CTACAGAAAGAAGCCCATGAAAAAGGACATGCAGGAGCCTCCTGCTGGCAAGG
AAGTGAAGAACGGCTTCAGCAAGGCTTATTTCACCGCCGCCAACGGAGTGATGA
ACAAGAAGGCACAG
```

-continued

---
SEQUENCE LISTING
---

SEQ ID NO: 3: Codon Variant 4 (CV4)
ATGGAACACCTGAAGGCATTCGACGACGAGATCAACGCCTTCCTGGATAACATG
TTCGGACCTAGAGATAGCAGAGTGCGGGGCTGGTTCATGCTGGACAGCTACCTG
CCTACCTTCTTCCTGACAGTGATGTACCTGCTGTCTATCTGGCTGGGCAACAAGT
ACATGAAAAATAGACCTGCCCTGAGCCTGCGGGGCATCCTCACACTGTACAACC
TGGGAATCACCCTGCTGAGCGCCTACATGCTGGCCGAGCTGATCCTGTCAACATG
GGAGGGCGGCTACAACCTGCAGTGCCAGGACCTGACCTCTGCCGGCGAGGCCGA
CATCAGAGTGGCCAAGGTGCTGTGGTGGTACTACTTTTCTAAGAGCGTGGAATTC
CTGGACACCATCTTCTTCGTGCTGAGAAAGAAGACCAGCCAGATCACATTCCTGC
ACGTGTACCACCACGCCAGCATGTTCAACATCTGGTGGTGCGTGCTGAACTGGAT
CCCCTGCGGCCAGAGCTTTTTCGGCCCTACACTGAACAGCTTCATCCACATCCTG
ATGTACAGCTATTACGGCCTGAGCGTGTTCCCCAGCATGCACAAGTACCTGTGGT
GGAAGAAATACCTGACACAGGCCCAGCTGGTGCAATTTGTGCTGACCATCACCC
ACACCATGAGCGCCGTGGTGAAACCTTGTGGATTTCCATTCGGCTGCCTGATTTT
CCAGTCTAGCTACATGCTGACCCTGGTCATCCTGTTCCTCAACTTCTACGTGCAG
ACCTACCGGAAGAAGCCCATGAAGAAGGACATGCAGGAGCCTCCTGCTGGCAA
GGAAGTGAAGAACGGCTTCAGCAAGGCTTATTTCACCGCCGCTAATGGCGTGAT
GAACAAGAAAGCCCAG SEQ ID NO: 4: Cytomegalovirus Promoter (CMV)
CTAGTTATTAATAGTAATCAATTACGGGGTCATTAGTTCATAGCCCATATATGGA
GTTCCGCGTTACATAACTTACGGTAAATGGCCCGCCTGGCTGACCGCCCAACGAC
CCCCGCCCATTGACGTCAATAATGACGTATGTTCCCATAGTAACGCCAATAGGG
ACTTTCCATTGACGTCAATGGGTGGACTATTTACGGTAAACTGCCCACTTGGCAG
TACATCAAGTGTATCATATGCCAAGTACGCCCCCTATTGACGTCAATGACGGTAA
ATGGCCCGCCTGGCATTATGCCCAGTACATGACCTTATGGGACTTTCCTACTTGG
CAGTACATCTACGTATTAGTCATCGCTATTACCATGGTGATGCGGTTTTGGCAGT
ACATCAATGGGCGTGGATAGCGGTTTGACTCACGGGGATTTCCAAGTCTCCACCC
CATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGG
GAGGTCTATATAAGCAGAGCTCTCTGGCTAACTAGAGAACCCACTGCTTACTGGC
TTATCGAAAT SEQ ID NO: 5: Adenovirus Tripartite Leader (ATL)
ACTCTCTTCCGCATCGCTGTCTGCGAGGGCCAGCTGTTGGGCTCGCGGTTGAGGA
CAAACTCTTCGCGGTCTTTCCAGTACTCTTGGATCGGAAACCCGTCGGCCTCCGA
ACGGTACTCCGCCACCGAGGGACCTGAGCGAGTCCGCATCGACCGGATCGGAAA
ACCTCTCGAGAAAGGCGTCTAACCAGTCACAGTCGCAAG SEQ ID NO: 6: Synthetic Intron
GTAGGCTGAGCACCGTGGCGGGCGGCAGCGGGTGGCGGTCGGGGTTGTTTCTGG
CGGAGGTGCTGCTGATGATGTAATTAAAGTAGGCGGTCTTGAGACGGCGGATGG
TCGAGGTGAGGTGTGGCAGGCTTGAGATCCAGCTGTTGGGGTGAGTACTCCCTCT
CAAAAGCGGGCATTACTTCTGCGCTAAGATTGTCAGTTTCCAAAAACGAGGAGG
ATTTGATATTCACCTGGCCCGATCTGGCCATACACTTGAGTGACAATGACATCCA
CTTTGCCTTTCTCTCCACAGGTGTCCACTCCCAG SEQ ID NO: 7: Human ELOVL2 Enhancer
TTGTTTTACTTTTGTTTCTGCCCTTCTTCCACTGTGACTAAATTTTTGCAATATAGA
AATAATACGGGCTTTGTGACCTTTAGCGTTTTCTTAGCTCTACAAATGTTGGAAA
ATGGATTTTGAACCTTAGCAAACAAGCTGAAACAGTTTAAACATTTGTTTGTGGG
TGCAGCAATGGAAGAAAGACTTCATTGGCATTTGTTATGATGGTGAGTACATTTG
TGAGATTAACATTCTTTGCTCAAGACTGAGAGGCCTCTGGTCAGCCGCCCCCATT
CTAAAGCAACACAGATCATATTCTGTCACACTGAGATCTCAGGTAACTGACCTTT
CTCACATCG SEQ ID NO: 8: Human Elongation Factor 1 Promoter (EF1)
ATCGATTGGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGC
GCGGGGTAAACTGGGAAAGTGATGTCGTGTACTGGCTCCGCCTTTTTCCCGAGGG
TGGGGGAGAACCGTATATAAGTGCAGTAGTCGCCGTGAACGTTCTTTTTCGCAAC
GGGTTTGCCGCCAGAACACAGGTGT SEQ ID NO: 9: P2A
CGCGCGAAGCGATCAGGCAGCGGGGCGACAAATTTCAGCCTTCTGAAACAAGCA
GGCGACGTGGAAGAAAACCCCGGTCCA SEQ ID NO: 10: GFP
ATGGTGTCCAAGGGCGAGGAACTGTTCACCGGCGTGGTGCCAATCCTGGTCGAG
CTGGACGGCGATGTGAATGGCCACAAGTTTTCTGTGTCTGGCGAAGGCGAGGGA
GATGCCACATACGGCAAGCTGACCCTGAAGTTCATCTGCACCACAGGAAAGTTG
CCTGTGCCCTGGCCTACCCTGGTGACCACCCTCACCTACGGCGTTCAGTGCTTCA
GCAGATACCCCGATCACATGAAACAGCACGACTTTTTCAAGTCCGCCATGCCTG
AGGGCTACGTGCAGGAGCGGACCATCTTCTTCAAAGACGACGGCAACTACAAGA
CAAGAGCCGAGGTGAAGTTCGAGGGCGACACCCTTGTGAACAGAATCGAGCTGA
AAGGCATCGACTTCAAGGAAGATGGAAATATCCTGGGCCACAAGCTGGAATACA

SEQUENCE LISTING

```
ACTACAACAGCCACAACGTGTACATCATGGCCGACAAGCAGAAGAACGGCATCA
AGGTGAACTTCAAGATCAGACACAACATCGAGGACGGCAGCGTGCAGCTGGCCG
ATCACTACCAGCAGAACACCCCTATCGGCGACGGCCCTGTGCTGCTGCCTGACA
ACCACTACCTGAGCACACAGAGCGCCCTGTCTAAGGACCCCAACGAGAAGAGAG
ATCACATGGTCCTGCTGGAATTCGTGACAGCCGCTGGCATAACACTCGGCATGG
ACGAGCTGTACAAGAGCGGCCTGAGAAGCCGGGCCCAGGCCAGCAACAGCGCC
GTGGACGGTACAGCCGGCCCCGGCTCTACCGGCAGCAGATAG

SEQ ID NO: 11: WPRE
TCCTGTTAATCAACCTCTGGATTACAAAATTTGTGAAAGATTGACTGATATTCTT
AACTATGTTGCTCCTTTTACGCTGTGTGGATATGCTGCTTTAATGCCTCTGTATCA
TGCTATTGCTTCCCGTACGGCTTTCGTTTTCTCCTCCTTGTATAAATCCTGGTTGCT
GTCTCTTTATGAGGAGTTGTGGCCCGTTGTCCGTCAACGTGGCGTGGTGTGCTCT
GTGTTTGCTGACGCAACCCCCACTGGCTGGGGCATTGCCACCACCTGTCAACTCC
TTTCTGGGACTTTCGCTTTCCCCCTCCCTATCGCCACGGCAGAACTCATCGCCGCC
TGCCTTGCCCGCTGCTGGACAGGGGCTAGGTTGCTGGGCACTGATAATTCCGTGG
TGTTGTCGGGGAAGCTGACGTC

SEQ ID NO: 12: Human Growth Hormone polyA
CTGCCCGGGTGGCATCCCTGTGACCCCTCCCCAGTGCCTCTCCTGGCCCTGGAAG
TTGCCACTCCAGTGCCCACCAGCCTTGTCCTAATAAAATTAAGTTGCATCATTTT
GTCTGACTAGGTGTCCTTCTATAATATTATGGGGTGGAGGGGGGTGGTATGGAGC
AAGGGGCCCAAGTTGGGAAGAAACCTGTAGGGCCTGCG SEQ ID NO: 13: AAV8-CMVT-CV4-GFP
GCGCGCTCGCTCGCTCACTGAGGCCGCCCGGGCAAAGCCCGGGCGTCGGGCGAC
CTTTGGTCGCCCGGCCTCAGTGAGCGAGCGAGCGCGCAGAGAGGGAGTGGCCAA
CTCCATCACTAGGGGTTCCTTGTAGTTAATGATTAACGGATCTTTACAAATTCAA
GCCAGGTGATTTCAACAAATTTTGCTGACGATTTAGGCGCACTATCCCCTAAACT
ACAAATTAGAAAATAGCGTTCCTTGACACTAGTTATTAATAGTAATCAATTACGG
GGTCATTAGTTCATAGCCCATATATGGAGTTCCGCGTTACATAACTTACGGTAAA
TGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAC
TATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTA
CATGACCTTATGGGACTTTCCTACTTGGCAGTACATCTACGTATTAGTCATCGCT
ATTACCATGGTGATGCGGTTTTGGCAGTACATCAATGGGCGTGGATAGCGGTTTG
ACTCACGGGGATTTCCAAGTCTCCACCCCATTGACGTCAATGGGAGTTTGTTTTG
GCACCAAAATCAACGGGACTTTCCAAAATGTCGTAACAACTCCGCCCCATTGAC
GCAAATGGGCGGTAGGCGTGTACGGTGGGAGGTCTATATAAGCAGAGCTCTCTG
GCTAACTAGAGAACCCACTGCTTACTGGCTTATCGAAATAAGCTTTCTCAGGGGA
GATCTCGTTTAGTGAACCGTCAGATCCTCACTCTCTTCCGCATCGCTGTCTGCGA
GGGCCAGCTGTTGGGCTCGCGGTTGAGGACAAACTCTTCGCGGTCTTTCCAGTAC
TCTTGGATCGGAAACCCGTCGGCCTCCGAACGGTACTCCGCCACCGAGGGACCT
GAGCGAGTCCGCATCGACCGGATCGGAAAACCTCTCGAGAAAGGCGTCTAACCA
GTCACAGTCGCAAGGTAGGCTGAGCACCGTGGCGGGCGGCAGCGGGTGGCGGTC
GGGGTTGTTTCTGGCGGAGGTGCTGCTGATGATGTAATTAAAGTAGGCGGTCTTG
AGACGGCGGATGGTCGAGGTGAGGTGTGGCAGGCTTGAGATCCAGCTGTTGGGG
TGAGTACTCCCTCTCAAAAGCGGGCATTACTTCTGCGCTAAGATTGTCAGTTTCC
AAAAACGAGGAGGATTTGATATTCACCTGGCCCGATCTGGCCATACACTTGAGT
GACAATGACATCCACTTTGCCTTTCTCTCCACAGGTGTCCACTCCCAGGTCCAAG
TTTAAACGCCGCCACCATGGAACACCTGAAGGCATTCGACGACGAGATCAACGC
CTTCCTGGATAACATGTTCGGACCTAGAGATAGCAGAGTGCGGGGCTGGTTCAT
GCTGGACAGCTACCTGCCTACCTTCTTCCTGACAGTGATGTACCTGCTGTCTATCT
GGCTGGGCAACAAGTACATGAAAAATAGACCTGCCCTGAGCCTGCGGGGCATCC
TCACACTGTACAACCTGGGAATCACCCTGCTGAGCGCCTACATGCTGGCCGAGCT
GATCCTGTCAACATGGGAGGGCGGCTACAACCTGCAGTGCCAGGACCTGACCTC
TGCCGGCGAGGCCGACATCAGAGTGGCCAAGGTGCTGTGGTGGTACTACTTTTCT
AAGAGCGTGGAATTCCTGGACACCATCTTCTTCGTGCTGAGAAAGAAGACCAGC
CAGATCACATTCCTGCACGTGTACCACCACGCCAGCATGTTCAACATCTGGTGGT
GCGTGCTGAACTGGATCCCCTGCGGCCAGAGCTTTTCGGCCCTACACTGAACAG
CTTCATCCACATCCTGATGTACAGCTATTACGGCCTGAGCGTGTTCCCCAGCATG
CACAAGTACCTGTGGTGGAAGAAATACCTGACACAGGCCCAGCTGGTGCAATTT
GTGCTGACCATCACCCACACCATGAGCGCCGTGGTGAAACCTTGTGGATTTCCAT
TCGGCTGCCTGATTTTCCAGTCTAGCTACATGCTGACCCTGGTCATCCTGTTCCTC
AACTTCTACGTGCAGACCTACCGGAAGAAGCCCATGAAGAAGGACATGCAGGA
GCCTCCTGCTGGCAAGGAAGTGAAGAACGGCTTCAGCAAGGCTTATTTCACCGC
CGCTAATGGCGTGATGAACAAGAAAGCCCAGCGCGCGAAGCGATCAGGCAGCG
GGGCGACAAATTTCAGCCTTCTGAAACAAGCAGGCGACGTGGAAGAAAACCCCG
GTCCAATGGTGTCCAAGGGCGAGGAACTGTTCACCGGCGTGGTGCCAATCCTGG
TCGAGCTGGACGGCGATGTGAATGGCCACAAGTTTTCTGTGTCTGGCGAAGGCG
AGGGAGATGCCACATACGGCAAGCTGACCCTGAAGTTCATCTGCACCACAGGAA
AGTTGCCTGTGCCCTGGCCTACCCTGGTGACCACCCTCACCTACGGCGTTCAGTG
CTTCAGCAGATACCCCGATCACATGAAACAGCACGACTTTTTCAAGTCCGCCATG
CCTGAGGGCTACGTGCAGGAGCGGACCATCTTCTTCAAAGACGACGGCAACTAC
AAGACAAGAGCCGAGGTGAAGTTCGAGGGCGACACCCTTGTGAACAGAATCGA
GCTGAAAGGCATCGACTTCAAGGAAGATGGAAATATCCTGGGCCACAAGCTGGA
```

```
ATACAACTACAACAGCCACAACGTGTACATCATGGCCGACAAGCAGAAGAACG
GCATCAAGGTGAACTTCAAGATCAGACACAACATCGAGGACGGCAGCGTGCAGC
TGGCCGATCACTACCAGCAGAACACCCCTATCGGCGACGGCCCTGTGCTGCTGC
CTGACAACCACTACCTGAGCACACAGAGCGCCCTGTCTAAGGACCCCAACGAGA
AGAGAGATCACATGGTCCTGCTGGAATTCGTGACAGCCGCTGGCATAACACTCG
GCATGGACGAGCTGTACAAGAGCGGCCTGAGAAGCCGGGCCCAGGCCAGCAAC
AGCGCCGTGGACGGTACAGCCGGCCCCGGCTCTACCGGCAGCAGATAGTCCTGT
TAATCAACCTCTGGATTACAAAATTTGTGAAAGATTGACTGATATTCTTAACTAT
GTTGCTCCTTTTACGCTGTGTGGATATGCTGCTTTAATGCCTCTGTATCATGCTAT
TGCTTCCCGTACGGCTTTCGTTTTCTCCTCCTTGTATAAATCCTGGTTGCTGTCTCT
TTATGAGGAGTTGTGGCCCGTTGTCCGTCAACGTGGCGTGGTGTGCTCTGTGTTT
GCTGACGCAACCCCCACTGGCTGGGGCATTGCCACCACCTGTCAACTCCTTTCTG
GGACTTTCGCTTTCCCCCTCCCTATCGCCACGGCAGAACTCATCGCCGCCTGCCT
TGCCCGCTGCTGGACAGGGGCTAGGTTGCTGGGCACTGATAATTCCGTGGTGTTG
TCGGGGAAGCTGACGTCCTGCCCGGGTGGCATCCCTGTGACCCCTCCCCAGTGCC
TCTCCTGGCCCTGGAAGTTGCCACTCCAGTGCCCACCAGCCTTGTCCTAATAAAA
TTAAGTTGCATCATTTTGTCTGACTAGGTGTCCTTCTATAATATTATGGGGTGGAG
GGGGGTGGTATGGAGCAAGGGGCCCAAGTTGGGAAGAAACCTGTAGGGCCTGC
GAGCGCTGGCTAGAATTACCTACCGGCCTCCACCATACCTTCGATATTCGCGCCC
ACTCTCCCATTAATCCGCACAAGTGGATGTGATGCGATTGCCCGCTAAGATAGTT
AATCATTAACTACAAGGAACCCCTAGTGATGGAGTTGGCCACTCCCTCTCTGCGC
GCTCGCTCGCTCACTGAGGCCGGGCGACCAAAGGTCGCCCGACGCCCGGGCTTT
GCCCGGGCGGCCTCAGTGAGCGAGCGAGCGCGC

SEQ ID NO: 14: MiniCircle CMVT-CV4-GFP
CTAGTTATTAATAGTAATCAATTACGGGGTCATTAGTTCATAGCCCATATATGGA
GTTCCGCGTTACATAACTTACGGTAAATGGCCCGCCTGGCTGACCGCCCAACGAC
CCCCGCCCATTGACGTCAATAATGACGTATGTTCCCATAGTAACGCCAATAGGG
ACTTTCCATTGACGTCAATGGGTGGACTATTTACGGTAAACTGCCCACTTGGCAG
TACATCAAGTGTATCATATGCCAAGTACGCCCCCTATTGACGTCAATGACGGTAA
ATGGCCCGCCTGGCATTATGCCCAGTACATGACCTTATGGGACTTTCCTACTTGG
CAGTACATCTACGTATTAGTCATCGCTATTACCATGGTGATGCGGTTTTGGCAGT
ACATCAATGGGCGTGGATAGCGGTTTGACTCACGGGGATTTCCAAGTCTCCACCC
CATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGG
GAGGTCTATATAAGCAGAGCTCTCTGGCTAACTAGAGAACCCACTGCTTACTGGC
TTATCGAAATAAGCTTTCTCAGGGGGATCTCGTTTAGTGAACCGTCAGATCCTC
ACTCTCTTCCGCATCGCTGTCTGCGAGGGCCAGCTGTTGGGCTCGCGGTTGAGGA
CAAACTCTTCGCGGTCTTTCCAGTACTCTTGGATCGGAAACCCGTCGGCCTCCGA
ACGGTACTCCGCCACCGAGGGACCTGAGCGAGTCCGCATCGACCGGATCGGAAA
ACCTCTCGAGAAAGGCGTCTAACCAGTCACAGTCGCAAGGTAGGCTGAGCACCG
TGGCGGGCGGCAGCGGGTGGCGGTCGGGGTTGTTTCTGGCGGAGGTGCTGCTGA
TGATGTAATTAAAGTAGGCGGTCTTGAGACGGCGGATGGTCGAGGTGAGGTGTG
GCAGGCTTGAGATCCAGCTGTTGGGGTGAGTACTCCCTCTCAAAAGCGGGCATT
ACTTCTGCGCTAAGATTGTCAGTTTCCAAAAACGAGGAGGATTTGATATTCACCT
GGCCCGATCTGGCCATACACTTGAGTGACAATGACATCCACTTTGCCTTTCTCTC
CACAGGTGTCCACTCCCAGGTCCAAGTTTAAACGCCGCCACCATGGAACACCTG
AAGGCATTCGACGACGAGATCAACGCCTTCCTGGATAACATGTTCGGACCTAGA
GATAGCAGAGTGCGGGGCTGGTTCATGCTGGACAGCTACCTGCCTACCTTCTTCC
TGACAGTGATGTACCTGCTGTCTATCTGGCTGGGCAACAAGTACATGAAAAATA
GACCTGCCCTGAGCCTGCGGGGCATCCTCACACTGTACAACCTGGGAATCACCCT
GCTGAGCGCCTACATGCTGGCCGAGCTGATCCTGTCAACATGGGAGGGCGGCTA
CAACCTGCAGTGCCAGGACCTGACCTCTGCCGGCGAGGCCGACATCAGAGTGGC
CAAGGTGCTGTGGTGGTACTACTTTTCTAAGAGCGTGGAATTCCTGGACACCATC
TTCTTCGTGCTGAGAAAGAAGACCAGCCAGATCACATTCCTGCACGTGTACCACC
ACGCCAGCATGTTCAACATCTGGTGGTGCGTGCTGAACTGGATCCCCTGCGGCCA
GAGCTTTTTCGGCCCTACACTGAACAGCTTCATCCACATCCTGATGTACAGCTAT
TACGGCCTGAGCGTGTTCCCCAGCATGCACAAGTACCTGTGGTGGAAGAAATAC
CTGACACAGGCCCAGCTGGTGCAATTTGTGCTGACCATCACCCACACCATGAGC
GCCGTGGTGAAACCTTGTGGATTTCCATTCGGCTGCCTGATTTTCCAGTCTAGCT
ACATGCTGACCCTGGTCATCCTGTTCCTCAACTTCTACGTGCAGACCTACCGGAA
GAAGCCCATGAAGAAGGACATGCAGGAGCCTCCTGCTGGCAAGGAAGTGAAGA
ACGGCTTCAGCAAGGCTTATTTCACCGCCGCTAATGGCGTGATGAACAAGAAAG
CCCAGCGCGCGAAGCGATCAGGCAGCGGGGCGACAAATTTCAGCCTTCTGAAAC
AAGCAGGCGACGTGGAAGAAACCCCGGTCCAATGGTGTCCAAGGGCGAGGAA
CTGTTCACCGGCGTGGTGCCAATCCTGGTCGAGCTGGACGGCGATGTGAATGGC
CACAAGTTTTCTGTGTCTGGCGAAGGCGAGGGAGATGCCACATACGGCAAGCTG
ACCCTGAAGTTCATCTGCACCACAGGAAAGTTGCCTGTGCCCTGGCCTACCCTGG
TGACCACCCTCACCTACGGCGTTCAGTGCTTCAGCAGATACCCCGATCACATGAA
ACAGCACGACTTTTTCAAGTCCGCCATGCCTGAGGGCTACGTGCAGGAGCGGAC
CATCTTCTTCAAAGACGACGGCAACTACAAGACAAGAGCCGAGGTGAAGTTCGA
GGGCGACACCCTTGTGAACAGAATCGAGCTGAAAGGCATCGACTTCAAGGAAGA
TGGAAATATCCTGGGGCACAAGCTGGAATACAACTACAACAGCCACAACGTGTA
CATCATGGCCGACAAGCAGAAGAACGGCATCAAGGTGAACTTCAAGATCAGAC
ACAACATCGAGGACGGCAGCGTGCAGCTGGCCGATCACTACCAGCAGAACACCC
CTATCGGCGACGGCCCTGTGCTGCTGCCTGACAACCACTACCTGAGCACACAGA
GCGCCCTGTCTAAGGACCCCAACGAGAAGAGAGATCACATGGTCCTGCTGGAAT
```

SEQUENCE LISTING

```
TCGTGACAGCCGCTGGCATAACACTCGGCATGGACGAGCTGTACAAGAGCGGCC
TGAGAAGCCGGGCCCAGGCCAGCAACAGCGCCGTGGACGGTACAGCCGGCCCC
GGCTCTACCGGCAGCAGATAGTCCTGTTAATCAACCTCTGGATTACAAAATTTGT
GAAAGATTGACTGATATTCTTAACTATGTTGCTCCTTTTACGCTGTGTGGATATGC
TGCTTTAATGCCTCTGTATCATGCTATTGCTTCCCGTACGGCTTTCGTTTTCTCCTC
CTTGTATAAATCCTGGTTGCTGTCTCTTTATGAGGAGTTGTGGCCCGTTGTCCGTC
AACGTGGCGTGGTGTGCTCTGTGTTTGCTGACGCAACCCCCACTGGCTGGGGCAT
TGCCACCACCTGTCAACTCCTTTCTGGGACTTTCGCTTTCCCCCTCCCTATCGCCA
CGGCAGAACTCATCGCCGCCTGCCTTGCCCGCTGCTGGACAGGGGCTAGGTTGCT
GGGCACTGATAATTCCGTGGTGTTGTCGGGGAAGCTGACGTCCTGCCCGGGTGG
CATCCCTGTGACCCCTCCCCAGTGCCTCTCCTGGCCCTGGAAGTTGCCACTCCAG
TGCCCACCAGCCTTGTCCTAATAAAATTAAGTTGCATCATTTTGTCTGACTAGGT
GTCCTTCTATAATATTATGGGGTGGAGGGGGGTGGTATGGAGCAAGGGGCCCAA
GTTGGGAAGAAACCTGTAGGGCCTGCG

Sequence ID 15 Human Rhodopsin Kinase Promoter
GGGCCCCAGAAGCCTGGTGGTTGTTTGTCCTTCTCAGGGGAAAAGTGAGGCGGC
CCCTTGGAGGAAGGGGCCGGGCAGAATGATCTAATCGGATTCCAAGCAGCTCAG
GGGATTGTCTTTTTCTAGCACCTTCTTGCCACTCCTAAGCGTCCTCCGTGACCCCG
GCTGGGATTTAGCCTGGTGCTGTGTCAGCCCCGGGCTCCCAGGGGCTTCCCAGTG
GTCCCCAGGAACCCTCGACAGGGCCAGGGCGTCTCTCTCGTCCAGCAAGGGCAG
GGACGGGCCACAGGCCAAGGGC Sequence ID 16 AAV8-HR-CMVT-CV4
GCGCGCTCGCTCGCTCACTGAGGCCGCCCGGGCAAAGCCCGGGCGTCGGGCGAC
CTTTGGTCGCCCGGCCTCAGTGAGCGAGCGAGCGCGCAGAGAGGGAGTGGCCAA
CTCCATCACTAGGGGTTCCTTGTAGTTAATGATTAACGGATCTTTACAAATTCAA
GCCAGGTGATTTCAACAAATTTTGCTGACGATTTAGGCGCACTATCCCCTAAACT
ACAAATTAGAAAATAGCGTTCCTTGACACTAGTTTGTTTTACTTTTGTTTCTGCCC
TTCTTCCACTGTGACTAAATTTTTGCAATATAGAAATAATACGGGCTTTGTGACC
TTTAGCGTTTTCTTAGCTCTACAAATGTTGGAAAATGGATTTTGAACCTTAGCAA
ACAAGCTGAAACAGTTTAAACATTTGTTTGTGGGTGCAGCAATGGAAGAAAGAC
TTCATTGGCATTTGTTATGATGGTGAGTACATTTGTGAGATTAACATTCTTTGCTC
AAGACTGAGAGGCCTCTGGTCAGCCGCCCCCATTCTAAAGCAACACAGATCATA
TTCTGTCACACTGAGATCTCAGGTAACTGACCTTTCTCACATCGACTAGTCTAGTT
ATTAATAGTAATCAATTACGGGGTCATTAGTTCATAGCCCATATATGGAGTTCCG
CGTTACATAACTTACGGTAAATGGCCCGCCTGGCTGACCGCCCAACGACCCCCG
CCCATTGACGTCAATAATGACGTATGTTCCCATAGTAACGCCAATAGGGACTTTC
CATTGACGTCAATGGGTGGACTATTTACGGTAAACTGCCCACTTGGCAGTACATC
AAGTGTATCATATGCCAAGTACGCCCCCTATTGACGTCAATGACGGTAAATGGCC
CGCCTGGCATTATGCCCAGTACATGACCTTATGGGACTTTCCTACTTGGCAGTAC
ATCTACGTATTAGTCATCGCTATTACCATGGTGATGCGGTTTTGGCAGTACATCA
ATGGGCGTGGATAGCGGTTTGACTCACGGGGATTTCCAAGTCTCCACCCCATTGA
CGTCAATGGGAGTTTGTTTTGGCACCAAAATCAACGGGACTTTCCAAAATGTCGT
AACAACTCCGCCCCATTGACGCAAATGGGCGGTAGGCGTGTACGGTGGGAGGTC
TATATAAGCAGAGCTCTCTGGCTAACTAGAGAACCCACTGCTTACTGGCTTATCG
AAATAAGCTTTCTCAGGGGAGATCTCGTTTAGTGAACCGTCAGATCCTCACTCTC
TTCCGCATCGCTGTCTGCGAGGGCCAGCTGTTGGGCTCGCGGTTGAGGACAAACT
CTTCGCGGTCTTTCCAGTACTCTTGGATCGGAAACCGTCGGCCTCCGAACGGTA
CTCCGCCACCGAGGGACCTGAGCGAGTCCGCATCGACCGGATCGGAAAACCTCT
CGAGAAAGGCGTCTAACCAGTCACAGTCGCAAGGTAGGCTGAGCACCGTGGCGG
GCGGCAGCGGGTGGCGGTCGGGGTTGTTTCTGGCGGAGGTGCTGCTGATGATGT
AATTAAAGTAGGCGGTCTTGAGACGGCGGATGGTCGAGGTGAGGTGTGGCAGGC
TTGAGATCCAGCTGTTGGGGTGAGTACTCCCTCTCAAAAGCGGGCATTACTTCTG
CGCTAAGATTGTCAGTTTCCAAAAACGAGGAGGATTTGATATTCACCTGGCCCGA
TCTGGCCATACACTTGAGTGACAATGACATCCACTTTGCCTTTCTCTCCACAGGT
GTCCACTCCCAGGTCCAAGTTTAAACGCCGCCACCATGGAACACCTGAAGGCAT
TCGACGACGAGATCAACGCCTTCCTGGATAACATGTTCGGACCTAGAGATAGCA
GAGTGCGGGGCTGGTTCATGCTGGACAGCTACCTGCCTACCTTCTTCCTGACAGT
GATGTACCTGCTGTCTATCTGGCTGGGCAACAAGTACATGAAAAATAGACCTGC
CCTGAGCCTGCGGGGCATCCTCACACTGTACAACCTGGGAATCACCCTGCTGAG
CGCCTACATGCTGGCCGAGCTGATCCTGTCAACATGGGAGGGCGGCTACAACCT
GCAGTGCCAGGACCTGACCTCTGCCGGCGAGGCCGACATCAGAGTGGCCAAGGT
GCTGTGGTGGTACTACTTTTCTAAGAGCGTGGAATTCCTGGACACCATCTTCTTC
GTGCTGAGAAAGAAGACCAGCCAGATCACATTCCTGCACGTGTACCACCACGCC
AGCATGTTCAACATCTGGTGGTGCGTGCTGAACTGGATCCCCTGCGGCCAGAGCT
TTTTCGGCCCTACACTGAACAGCTTCATCCACATCCTGATGTACAGCTATTACGG
CCTGAGCGTGTTCCCCAGCATGCACAAGTACCTGTGGTGGAAGAAATACCTGAC
ACAGGCCCAGCTGGTGCAATTTGTGCTGACCATCACCCACACCATGAGCGCCGT
GGTGAAACCTTGTGGATTTCCATTCGGCTGCCTGATTTTCCAGTCTAGCTACATG
CTGACCCTGGTCATCCTGTTCCTCAACTTCTACGTGCAGACCTACCGGAAGAAGC
CCATGAAGAAGGACATGCAGGAGCCTCCTGCTGGCAAGGAAGTGAAGAACGGC
TTCAGCAAGGCTTATTTCACCGCCGCTAATGGCGTGATGAACAAGAAAGCCCAG
TAGTCCTGTTAATCAACCTCTGGATTACAAAATTTGTGAAAGATTGACTGATATT
CTTAACTATGTTGCTCCTTTTACGCTGTGTGGATATGCTGCTTTAATGCCTCTGTA
TCATGCTATTGCTTCCCGTACGGCTTTCGTTTTCTCCTCCTTGTATAAATCCTGGTT
GCTGTCTCTTTATGAGGAGTTGTGGCCCGTTGTCCGTCAACGTGGCGTGGTGTGC
```

```
TCTGTGTTTGCTGACGCAACCCCCACTGGCTGGGGCATTGCCACCACCTGTCAAC
TCCTTTCTGGGACTTTCGCTTTCCCCCTCCCTATCGCCACGGCAGAACTCATCGCC
GCCTGCCTTGCCCGCTGCTGGACAGGGGCTAGGTTGCTGGGCACTGATAATTCCG
TGGTGTTGTCGGGGAAGCTGACGTCCTGCCCGGGTGGCATCCCTGTGACCCCTCC
CCAGTGCCTCTCCTGGCCCTGGAAGTTGCCACTCCAGTGCCCACCAGCCTTGTCC
TAATAAAATTAAGTTGCATCATTTTGTCTGACTAGGTGTCCTTCTATAATATTATG
GGGTGGAGGGGGGTGGTATGGAGCAAGGGGCCCAAGTTGGGAAGAAACCTGTA
GGGCCTGCGAGCGCTGGCTAGAATTACCTACCGGCCTCCACCATACCTTCGATAT
TCGCGCCCACTCTCCCATTAATCCGCACAAGTGGATGTGATGCGATTGCCCGCTA
AGATAGTTAATCATTAACTACAAGGAACCCCTAGTGATGGAGTTGGCCACTCCCT
CTCTGCGCGCTCGCTCGCTCACTGAGGCCGGGCGACCAAAGGTCGCCCGACGCC
CGGGCTTTGCCCGGGCGGCCTCAGTGAGCGAGCGAGCGCGC
```

Sequence ID 17 AAV8-HR-hRKT-CV4
```
GCGCGCTCGCTCGCTCACTGAGGCCGCCCGGGCAAAGCCCGGGCGTCGGGCGAC
CTTTGGTCGCCCGGCCTCAGTGAGCGAGCGAGCGCGCAGAGAGGGAGTGGCCAA
CTCCATCACTAGGGGTTCCTTGTAGTTAATGATTAACGGATCTTTACAAATTCAA
GCCAGGTGATTTCAACAAATTTTGCTGACGATTTAGGCGCACTATCCCCTAAACT
ACAAATTAGAAAATAGCGTTCCTTGACACTAGTTTGTTTTACTTTTGTTTCTGCCC
TTCTTCCACTGTGACTAAATTTTTGCAATATAGAAATAATACGGGCTTTGTGACC
TTTAGCGTTTTCTTAGCTCTACAAATGTTGGAAAATGGATTTTGAACCTTAGCAA
ACAAGCTGAAACAGTTTAAACATTTGTTTGTGGGTGCAGCAATGGAAGAAAGAC
TTCATTGGCATTTGTTATGATGGTGAGTACATTTGTGAGATTAACATTCTTTGCTC
AAGACTGAGAGGCCTCTGGTCAGCCGCCCCCATTCTAAAGCAACACAGATCATA
TTCTGTCACACTGAGATCTCAGGTAACTGACCTTTCTCACATCGACTAGTGCGGC
CGCGGGCCCCAGAAGCCTGGTGGTTGTTTGTCCTTCTCAGGGGAAAAGTGAGGC
GGCCCCTTGGAGGAAGGGGCCGGGCAGAATGATCTAATCGGATTCCAAGCAGCT
CAGGGGATTGTCTTTTTCTAGCACCTTCTTGCCACTCCTAAGCGTCCTCCGTGACC
CCGGCTGGGATTTAGCCTGGTGCTGTGTCAGCCCCGGGCTCCCAGGGGCTTCCCA
GTGGTCCCCAGGAACCCTCGACAGGGCCAGGGCGTCTCTCTCGTCCAGCAAGGG
CAGGGACGGGCCACAGGCCAAGGGCAAGCTTTCTCAGGGGAGATCTCGTTTAGT
GAACCGTCAGATCCTCACTCTCTTCCGCATCGCTGTCTGCGAGGGCCAGCTGTTG
GGCTCGCGGTTGAGGACAAACTCTTCGCGGTCTTTCCAGTACTCTTGGATCGGAA
ACCCGTCGGCCTCCGAACGGTACTCCGCCACCGAGGGACCTGAGCGAGTCCGCA
TCGACCGGATCGGAAAACCTCTCGAGAAAGGCGTCTAACCAGTCACAGTCGCAA
GGTAGGCTGAGCACCGTGGCGGGCGGCAGCGGGTGGCGGTCGGGGTTGTTTCTG
GCGGAGGTGCTGCTGATGATGTAATTAAAGTAGGCGGTCTTGAGACGGCGGATG
GTCGAGGTGAGGTGTGGCAGGCTTGAGATCCAGCTGTTGGGGTGAGTACTCCCT
CTCAAAAGCGGGCATTACTTCTGCGCTAAGATTGTCAGTTTCCAAAAACGAGGA
GGATTTGATATTCACCTGGCCCGATCTGGCCATACACTTGAGTGACAATGACATC
CACTTTGCCTTTCTCTCCACAGGTGTCCACTCCCAGGTCCAAGTTTAAACGCCGC
CACCATGGAACACCTGAAGGCATTCGACGACGAGATCAACGCCTTCCTGGATAA
CATGTTCGGACCTAGAGATAGCAGAGTGCGGGGCTGGTTCATGCTGGACAGCTA
CCTGCCTACCTTCTTCCTGACAGTGATGTACCTGCTGTCTATCTGGCTGGGCAAC
AAGTACATGAAAAATAGACCTGCCCTGAGCCTGCGGGGCATCCTCACACTGTAC
AACCTGGGAATCACCCTGCTGAGCGCCTACATGCTGGCCGAGCTGATCCTGTCA
ACATGGGAGGGCGGCTACAACCTGCAGTGCCAGGACCTGACCTCTGCCGGCGAG
GCCGACATCAGAGTGGCCAAGGTGCTGTGGTGGTACTACTTTTCTAAGAGCGTG
GAATTCCTGGACACCATCTTCTTCGTGCTGAGAAAGAAGACCAGCCAGATCACA
TTCCTGCACGTGTACCACCACGCCAGCATGTTCAACATCTGGTGGTGCGTGCTGA
ACTGGATCCCCTGCGGCCAGAGCTTTTTCGGCCCTACACTGAACAGCTTCATCCA
CATCCTGATGTACAGCTATTACGGCCTGAGCGTGTTCCCCAGCATGCACAAGTAC
CTGTGGTGGAAGAAATACCTGACACAGGCCCAGCTGGTGCAATTTGTGCTGACC
ATCACCCACACCATGAGCGCCGTGGTGAAACCTTGTGGATTTCCATTCGGCTGCC
TGATTTTCCAGTCTAGCTACATGCTGACCCTGGTCATCCTGTTCCTCAACTTCTAC
GTGCAGACCTACCGGAAGAAGCCCATGAAGAAGGACATGCAGGAGCCTCCTGCT
GGCAAGGAAGTGAAGAACGGCTTCAGCAAGGCTTATTTCACCGCCGCTAATGGC
GTGATGAACAAGAAAGCCCAGTAGTCCTGTTAATCAACCTCTGGATTACAAAAT
TTGTGAAAGATTGACTGATATTCTTAACTATGTTGCTCCTTTTACGCTGTGTGGAT
ATGCTGCTTTAATGCCTCTGTATCATGCTATTGCTTCCCGTACGGCTTTCGTTTTC
TCCTCCTTGTATAAATCCTGGTTGCTGTCTCTTTATGAGGAGTTGTGGCCCGTTGT
CCGTCAACGTGGCGTGGTGTGCTCTGTGTTTGCTGACGCAACCCCCACTGGCTGG
GGCATTGCCACCACCTGTCAACTCCTTTCTGGGACTTTCGCTTTCCCCCTCCCTAT
CGCCACGGCAGAACTCATCGCCGCCTGCCTTGCCCGCTGCTGGACAGGGGCTAG
GTTGCTGGGCACTGATAATTCCGTGGTGTTGTCGGGGAAGCTGACGTCCTGCCCG
GGTGGCATCCCTGTGACCCCTCCCCAGTGCCTCTCCTGGCCCTGGAAGTTGCCAC
TCCAGTGCCCACCAGCCTTGTCCTAATAAAATTAAGTTGCATCATTTTGTCTGACT
AGGTGTCCTTCTATAATATTATGGGGTGGAGGGGGGTGGTATGGAGCAAGGGGT
CCAAGTTGGGAAGAAACCTGTAGGGCCTGCGAGCGCTGGCTAGAATTACCTACC
GGCCTCCACCATACCTTCGATATTCGCGCCCACTCTCCCATTAATCCGCACAAGT
GGATGTGATGCGATTGCCCGCTAAGATAGTTAATCATTAACTACAAGGAACCCCT
AGTGATGGAGTTGGCCACTCCCTCTCTGCGCGCTCGCTCGCTCACTGAGGCCGGG
CGACCAAAGGTCGCCCGACGCCCGGGCTTTGCCCGGGCGGCCTCAGTGAGCGAG
CGAGCGCGC
```

-continued

---

SEQUENCE LISTING

---

Sequence ID 18 AAV8-HR-EF1aT-CV4
GCGCGCTCGCTCGCTCACTGAGGCCGCCCGGGCAAAGCCCGGGCGTCGGGCGAC
CTTTGGTCGCCCGGCCTCAGTGAGCGAGCGAGCGCGCAGAGAGGGAGTGGCCAA
CTCCATCACTAGGGGTTCCTTGTAGTTAATGATTAACGGATCTTTACAAATTCAA
GCCAGGTGATTTCAACAAATTTTGCTGACGATTTAGGCGCACTATCCCCTAAACT
ACAAATTAGAAAATAGCGTTCCTTGACACTAGTTTGTTTTACTTTTGTTTCTGCCC
TTCTTCCACTGTGACTAAATTTTTGCAATATAGAAATAATACGGGCTTTGTGACC
TTTAGCGTTTTCTTAGCTCTACAAATGTTGGAAATGGATTTTGAACCTTAGCAA
ACAAGCTGAAACAGTTTAAACATTTGTTTGTGGGTGCAGCAATGGAAGAAAGAC
TTCATTGGCATTTGTTATGATGGTGAGTACATTTGTGAGATTAACATTCTTTGCTC
AAGACTGAGAGGCCTCTGGTCAGCCGCCCCCATTCTAAAGCAACACAGATCATA
TTCTGTCACACTGAGATCTCAGGTAACTGACCTTTCTCACATCGACTAGTGCGGC
CGCATCGATTGGCTCCGGTGCCCGTCAGTGGGCAGAGCGCACATCGCCCACAGT
CCCCGAGAAGTTGGGGGGAGGGGTCGGCAATTGAACCGGTGCCTAGAGAAGGT
GGCGCGGGGTAAACTGGGAAAGTGATGTCGTGTACTGGCTCCGCCTTTTTCCCGA
GGGTGGGGGAGAACCGTATATAAGTGCAGTAGTCGCCGTGAACGTTCTTTTTCGC
AACGGGTTTGCCGCCAGAACACAGGTGTAAGCTTTCTCAGGGGAGATCTCGTTTA
GTGAACCGTCAGATCCTCACTCTCTTCCGCATCGCTGTCTGCGAGGGCCAGCTGT
TGGGCTCGCGGTTGAGGACAAACTCTTCGCGGTCTTTCCAGTACTCTTGGATCGG
AAACCCGTCGGCCTCCGAACGGTACTCCGCCACCGAGGGACCTGAGCGAGTCCG
CATCGACCGGATCGGAAAACCTCTCGAGAAAGGCGTCTAACCAGTCACAGTCGC
AAGGTAGGCTGAGCACCGTGGCGGGCGGCAGCGGGTGGCGGTCGGGGTTGTTTC
TGGCGGAGGTGCTGCTGATGATGTAATTAAAGTAGGCGGTCTTGAGACGGCGGA
TGGTCGAGGTGAGGTGTGGCAGGCTTGAGATCCAGCTGTTGGGGTGAGTACTCC
CTCTCAAAAGCGGGCATTACTTCTGCGCTAAGATTGTCAGTTTCCAAAAACGAGG
AGGATTTGATATTCACCTGGCCCGATCTGGCCATACACTTGAGTGACAATGACAT
CCACTTTGCCTTTCTCTCCACAGGTGTCCACTCCCAGGTCCAAGTTTAAACGCCG
CCACCATGGAACACCTGAAGGCATTCGACGACGAGATCAACGCCTTCCTGGATA
ACATGTTCGGACCTAGAGATAGCAGAGTGCGGGGCTGGTTCATGCTGGACAGCT
ACCTGCCTACCTTCTTCCTGACAGTGATGTACCTGCTGTCTATCTGGCTGGGCAA
CAAGTACATGAAAAATAGACCTGCCCTGAGCCTGCGGGGCATCCTCACACTGTA
CAACCTGGGAATCACCCTGCTGAGCGCCTACATGCTGGCCGAGCTGATCCTGTCA
ACATGGGAGGGCGGCTACAACCTGCAGTGCCAGGACCTGACCTCTGCCGGCGAG
GCCGACATCAGAGTGGCCAAGGTGCTGTGGTGGTACTACTTTTCTAAGAGCGTG
GAATTCCTGGACACCATCTTCTTCGTGCTGAGAAAGAAGACCAGCCAGATCACA
TTCCTGCACGTGTACCACCACGCCAGCATGTTCAACATCTGGTGGTGCGTGCTGA
ACTGGATCCCCTGCGGCCAGAGCTTTTTCGGCCCTACACTGAACAGCTTCATCCA
CATCCTGATGTACAGCTATTACGGCCTGAGCGTGTTCCCCAGCATGCACAAGTAC
CTGTGGTGGAAGAAATACCTGACACAGGCCCAGCTGGTGCAATTTGTGCTGACC
ATCACCCACACCATGAGCGCCGTGGTGAAACCTTGTGGATTTCCATTCGGCTGCC
TGATTTTCCAGTCTAGCTACATGCTGACCCTGGTCATCCTGTTCCTCAACTTCTAC
GTGCAGACCTACCGGAAGAAGCCCATGAAGAAGGACATGCAGGAGCCTCCTGCT
GGCAAGGAAGTGAAGAACGGCTTCAGCAAGGCTTATTTCACCGCCGCTAATGGC
GTGATGAACAAGAAAGCCCAGTAGTCCTGTTAATCAACCTCTGGATTACAAAAT
TTGTGAAAGATTGACTGATATTCTTAACTATGTTGCTCCTTTTACGCTGTGTGGAT
ATGCTGCTTTAATGCCTCTGTATCATGCTATTGCTTCCCGTACGGCTTTCGTTTTC
TCCTCCTTGTATAAATCCTGGTTGCTGTCTCTTTATGAGGAGTTGTGGCCCGTTGT
CCGTCAACGTGGCGTGGTGTGCTCTGTGTTTGCTGACGCAACCCCCACTGGCTGG
GGCATTGCCACCACCTGTCAACTCCTTTCTGGGACTTTCGCTTTCCCCCTCCCTAT
CGCCACGGCAGAACTCATCGCCGCCTGCCTTGCCCGCTGCTGGACAGGGGCTAG
GTTGCTGGGCACTGATAATTCCGTGGTGTTGTCGGGGAAGCTGACGTCCTGCCCG
GGTGGCATCCCTGTGACCCCTCCCCAGTGCCTCTCCTGGCCCTGGAAGTTGCCAC
TCCAGTGCCCACCAGCCTTGTCCTAATAAAATTAAGTTGCATCATTTTGTCTGACT
AGGTGTCCTTCTATAATATTATGGGGTGGAGGGGGGTGGTATGGAGCAAGGGGC
CCAAGTTGGGAAGAAACCTGTAGGGCCTGCGAGCGCTGGCTAGAATTACCTACC
GGCCTCCACCATACCTTCGATATTCGCGCCCACTCTCCCATTAATCCGCACAAGT
GGATGTGATGCGATTGCCCGCTAAGATAGTTAATCATTAACTACAAGGAACCCCT
AGTGATGGAGTTGGCCACTCCCTCTCTGCGCGCTCGCTCGCTCACTGAGGCCGGG
CGACCAAAGGTCGCCCGACGCCCGGGCTTTGCCCGGGCGGCCTCAGTGAGCGAG
CGAGCGCGC Sequence ID 19 AAV8 Wild Type Capsid
MAADGYLPDWLEDNLSEGIREWWALKPGAPKPKANQQKQDDGRGLVLPGYKYLG
PFNGLDKGEPVNAADAAALEHDKAYDQQLQAGDNPYLRYNHADAEFQERLQEDTS
FGGNLGRAVFQAKKRVLEPLGLVEEGAKTAPGKKRPVEPSPQRSPDSSTGIGKKGQQ
PARKRLNFGQTGDSESVPDPQPLGEPPAAPSGVGPNTMAAGGGAPMADNNEGADG
VGSSSGNWHCDSTWLGDRVITTSTRTWALPTYNNHLYKQISNGTSGGATNDNTYFG
YSTPWGYFDFNRFHCHFSPRDWQRLINNNWGFRPKRLSFKLFNIQVKEVTQNEGTK
TIANNLTSTIQVFTDSEYQLPYVLGSAHQGCLPPFPADVFMIPQYGYLTLNNGSQAV
GRSSFYCLEYFPSQMLRTGNNFQFTYTFEDVPFHSSYAHSQSLDRLMNPLIDQYLYY
LSRTQTTGGTANTQTLGFSQGGPNTMANQAKNWLPGPCYRQQRVSTTTGQNNNSN
FAWTAGTKYHLNGRNSLANPGIAMATHKDDEERFFPSNGILIFGKQNAARDNADYS
DVMLTSEEEIKTTNPVATEEYGIVADNLQQQNTAPQIGTVNSQGALPGMVWQNRDV
YLQGPIWAKIPHTDGNFHPSPLMGGFGLKHPPPQILIKNTPVPADPPTTFNQSKLNSFI
TQYSTGQVSVEIEWELQKENSKRWNPEIQYTSNYYKSTSVDFAVNTEGVYSEPRPIG
TRYLTRNL

SEQUENCE LISTING

Sequence ID 20 AAV8-Y447F Capsid
MAADGYLPDWLEDNLSEGIREWWALKPGAPKPKANQQKQDDGRGLVLPGYKYLG
PFNGLDKGEPVNAADAAALEHDKAYDQQLQAGDNPYLRYNHADAEFQERLQEDTS
FGGNLGRAVFQAKKRVLEPLGLVEEGAKTAPGKKRPVEPSPQRSPDSSTGIGKKGQQ
PARKRLNFGQTGDSESVPDPQPLGEPPAAPSGVGPNTMAAGGGAPMADNNEGADG
VGSSSGNWHCDSTWLGDRVITTSTRTWALPTYNNHLYKQISNGTSGGATNDNTYFG
YSTPWGYFDFNRFHCHFSPRDWQRLINNNWGFRPKRLSFKLFNIQVKEVTQNEGTK
TIANNLTSTIQVFTDSEYQLPYVLGSAHQGCLPPFPADVFMIPQYGYLTLNNGSQAV
GRSSFYCLEYFPSQMLRTGNNFQFTYTFEDVPFHSSYAHSQSLDRLMNPLIDQYLYFL
SRTQTTGGTANTQTLGFSQGGPNTMANQAKNWLPGPCYRQQRVSTTTGQNNNSNF
AWTAGTKYHLNGRNSLANPGIAMATHKDDEERFFPSNGILIFGKQNAARDNADYSD
VMLTSEEEIKTTNPVATEEYGIVADNLQQQNTAPQIGTVNSQGALPGMVWQNRDVY
LQGPIWAKIPHTDGNFHPSPLMGGFGLKHPPPQILIKNTPVPADPPTTFNQSKLNSFIT
QYSTGQVSVEIEWELQKENSKRWNPEIQYTSNYYKSTSVDFAVNTEGVYSEPRPIGT
RYLTRNL Sequence ID 21 AAV8-Y733F Capsid
MAADGYLPDWLEDNLSEGIREWWALKPGAPKPKANQQKQDDGRGLVLPGYKYLG
PFNGLDKGEPVNAADAAALEHDKAYDQQLQAGDNPYLRYNHADAEFQERLQEDTS
FGGNLGRAVFQAKKRVLEPLGLVEEGAKTAPGKKRPVEPSPQRSPDSSTGIGKKGQQ
PARKRLNFGQTGDSESVPDPQPLGEPPAAPSGVGPNTMAAGGGAPMADNNEGADG
VGSSSGNWHCDSTWLGDRVITTSTRTWALPTYNNHLYKQISNGTSGGATNDNTYFG
YSTPWGYFDFNRFHCHFSPRDWQRLINNNWGFRPKRLSFKLFNIQVKEVTQNEGTK
TIANNLTSTIQVFTDSEYQLPYVLGSAHQGCLPPFPADVFMIPQYGYLTLNNGSQAV
GRSSFYCLEYFPSQMLRTGNNFQFTYTFEDVPFHSSYAHSQSLDRLMNPLIDQYLYY
LSRTQTTGGTANTQTLGFSQGGPNTMANQAKNWLPGPCYRQQRVSTTTGQNNNSN
FAWTAGTKYHLNGRNSLANPGIAMATHKDDEERFFPSNGILIFGKQNAARDNADYS
DVMLTSEEEIKTTNPVATEEYGIVADNLQQQNTAPQIGTVNSQGALPGMVWQNRDV
YLQGPIWAKIPHTDGNFHPSPLMGGFGLKHPPPQILIKNTPVPADPPTTFNQSKLNSFI
TQYSTGQVSVEIEWELQKENSKRWNPEIQYTSNYYKSTSVDFAVNTEGVYSEPRPIG
TRFLTRNL Sequence ID 22 AAV8-Y447F + Y733F Capsid
MAADGYLPDWLEDNLSEGIREWWALKPGAPKPKANQQKQDDGRGLVLPGYKYLG
PFNGLDKGEPVNAADAAALEHDKAYDQQLQAGDNPYLRYNHADAEFQERLQEDTS
FGGNLGRAVFQAKKRVLEPLGLVEEGAKTAPGKKRPVEPSPQRSPDSSTGIGKKGQQ
PARKRLNFGQTGDSESVPDPQPLGEPPAAPSGVGPNTMAAGGGAPMADNNEGADG
VGSSSGNWHCDSTWLGDRVITTSTRTWALPTYNNHLYKQISNGTSGGATNDNTYFG
YSTPWGYFDFNRFHCHFSPRDWQRLINNNWGFRPKRLSFKLFNIQVKEVTQNEGTK
TIANNLTSTIQVFTDSEYQLPYVLGSAHQGCLPPFPADVFMIPQYGYLTLNNGSQAV
GRSSFYCLEYFPSQMLRTGNNFQFTYTFEDVPFHSSYAHSQSLDRLMNPLIDQYLYFL
SRTQTTGGTANTQTLGFSQGGPNTMANQAKNWLPGPCYRQQRVSTTTGQNNNSNF
AWTAGTKYHLNGRNSLANPGIAMATHKDDEERFFPSNGILIFGKQNAARDNADYSD
VMLTSEEEIKTTNPVATEEYGIVADNLQQQNTAPQIGTVNSQGALPGMVWQNRDVY
LQGPIWAKIPHTDGNFHPSPLMGGFGLKHPPPQILIKNTPVPADPPTTFNQSKLNSFIT
QYSTGQVSVEIEWELQKENSKRWNPEIQYTSNYYKSTSVDFAVNTEGVYSEPRPIGT
RFLTRNL

What is claimed is:

1. A method of treating age-related macular degeneration (AMD), comprising:
   administering a composition comprising a polynucleotide sequence comprising SEQ ID NO: 3 to the eye of a subject, wherein the polynucleotide is operably linked to a promoter and administered to the eye by an intravitreal or subretinal injection.

2. The method of claim 1, wherein the composition is administered at a dose at about 5×10⁷ vg/eye to about 9×10¹¹ vg/eye.

3. The method of claim 1, further comprising administering an additional therapeutic agent selected from a corticosteroid, an anti-inflammation agent, a demethylating agent, or a combination thereof.

4. The method of claim 3, wherein the demethylating agent is decitabine.

5. The method of claim 1, wherein the polynucleotide sequence further comprises, or is linked to, an enhancer, an inverted terminal repeat (ITR), polyadenylation signal, a signal sequence, or a combination thereof.

6. The method of claim 1, wherein the polynucleotide sequence further comprises, or is linked to, a cytomegalovirus (CMV) promoter, an adenovirus tripartite leader (ATL)

sequence, a synthetic intron, a human ELOVL2 enhancer sequence, a human elongation factor 1-alpha (EF1a) promoter, a woodchuck hepatitis posttranscriptional regulatory element (wpre element), a human growth hormone polyA tail, or a human rhodopsin kinase promoter.

7. The method of claim 1, wherein the polynucleotide sequence further comprises, or is linked to, a nucleotide sequence selected from SEQ ID NO: 4, SEQ ID NO: 5, SEQ ID NO: 6, SEQ ID NO: 7, SEQ ID NO: 8, SEQ ID NO: 9, SEQ ID NO: 11, SEQ ID NO: 12, and SEQ ID NO: 15.

8. The method of claim 1, wherein the composition comprises a viral capsid or an envelope.

9. The method of claim 8, wherein the viral capsid is an adeno-associated virus (AAV) based capsid.

10. The method of claim 9, wherein the AAV based capsid comprises a AAV-serotype 8 (AAV8) based capsid.

11. The method of claim 9, wherein the AAV based capsid has an amino acid sequence selected from SEQ ID NO: 19, SEQ ID NO: 20, SEQ ID NO: 21, and SEQ ID NO: 22.

12. The method of claim 1, wherein the composition further comprises a non-viral delivery system.

13. The method of claim 1, wherein the polynucleotide sequence is in a DNA minicircle.

* * * * *

SEQUENCE LISTING

Sequence total quantity: 22
SEQ ID NO: 1              moltype = DNA   length = 888
FEATURE                   Location/Qualifiers
source                    1..888
                          mol_type = other DNA
                          organism = Adenovirus
SEQUENCE: 1
atggaacatc taaaggcctt tgatgatgaa atcaatgctt ttttggacaa tatgtttgga    60
ccgcgagatt ctcgagtcag agggtggttc atgttggaat cttaccttcc tacctttttt   120
cttactgtca tgtatctgct ctcaaatatgg ctgggtaaca agtatatgaa gaacagacct   180
gctctttctc tcaggggtat cctcaccttg tataatcttg gaatcacact tctctccgcg   240
tacatgctgg cagagctcat tctctccact tgggaaggag gctacaactt acagtgtcaa   300
gatcttacca gcgcagggga agctgacatc cgggtagcca aggtgctttg gtggtactat   360
ttctccaaat cagtagagtt cctggacaca attttcttcg tttttcggaa aaaaacgagt   420
cagattactt ttcttcatgt atatcatcat gcttctatgt ttaacatctg gtggtgtgtc   480
ttgaactgga taccttgtgg acaaagtttc tttggaccaa cactgaacag tttttatccac   540
attcttatgt actcctacta tggactttct gtgtttccat ctatgcacaa gtatctttgg   600
tggaagaaat atctcacaca ggctcagctg gtgcagttcg tgctcaccat cacgcacacc   660
atgagcgccg tcgtgaaacc gtgtggcttc cccttcggtt gtctcatctt ccagtcatct   720
tatatgctaa cgttagtcat cctcttctta aatttttacg ttcagacata ccgaaaaaag   780
ccaatgaaga aagatatgca agagccacct gcagggaaag aagtgaagaa tggttttttcc   840
aaagcctact tcactgcagc aaatggagtg atgaacaaga aagcacaa               888

-continued

```
SEQ ID NO: 2            moltype = DNA   length = 888
FEATURE                 Location/Qualifiers
source                  1..888
                        mol_type = other DNA
                        organism = Adenovirus
SEQUENCE: 2
atggaacacc tgaaggcctt cgacgacgag atcaacgcct ttctggacaa catgttcggc    60
cccagagatt ctagagtgcg gggctggttc atgctggata gctacctgcc tacattcttc   120
ctgaccgtga tgtacctgct gagcatcctg ctgggcaaca agtacatgaa aaacagacct   180
gccctgagcc tgagaggcat cctgaccctg tacaacctgg gaattacact gctgagcgcc   240
tacatgctgg ccgagctgat cctgtcaaca tgggagggcg gctacaacct gcagtgccag   300
gacctgacct ccgccggcga ggccgacatc agagtggcca aggtgctgtg gtggtactac   360
ttcagcaaaa gcgtggaatt cctggacacc atcttcttcg tgctgcggaa gaagaccagc   420
cagatcacct tcctgcacgt gtaccaccac gccagcatgt tcaacatctg gtggtgcgtg   480
ctgaattgga tcccctgcgg ccagtctttt tttggaccta cccttaatag cttcatccac   540
atcctgatgt actcttatta cggcctgtct gtttttcccat ctatgcacaa gtacctgtgg   600
tggaagaaat acctgacaca ggcccagctg gtccagttcg tgctcacaat cacccacacc   660
atgagcgccg tggtgaagcc ttgtggcttt ccattcggtt gtctgatctt tcagagcagc   720
tacatgctga cactggtgat cctgttcctg aacttctacg tgcagaccta cagaaagaag   780
cccatgaaaa aggacatgca ggagcctcct gctggcaagg aagtgaagaa cggcttcagc   840
aaggcttatt tcaccgccgc caacggagtg atgaacaaga aggcacag                888

SEQ ID NO: 3            moltype = DNA   length = 888
FEATURE                 Location/Qualifiers
source                  1..888
                        mol_type = other DNA
                        organism = Adenovirus
SEQUENCE: 3
atggaacacc tgaaggcatt cgacgacgag atcaacgcct tcctggataa catgttcgga    60
cctagagata gcagagtgcg gggctggttc atgctggaca gctacctgcc taccttcttc   120
ctgacagtga tgtacctgct gtctatctgg ctgggcaaca agtacatgaa aaatagacct   180
gccctgagcc tgcggggcat cctcacactg tacaacctgg gaatcaccct gctgagcgcc   240
tacatgctgg ccgagctgat cctgtcaaca tgggagggcg gctacaacct gcagtgccag   300
gacctgacct ctgccggcga ggccgacatc agagtggcca aggtgctgtg gtggtactac   360
ttttctaaga gcgtggaatt cctggacacc atcttcttcg tgctgagaaa gaagaccagc   420
cagatcacat tcctgcacgt gtaccaccac gccagcatgt tcaacatctg gtggtgcgtg   480
ctgaactgga tcccctgcgg ccagagcttt ttcggcccta cactgaacag cttcatccac   540
atcctgatgt acagctatta cggcctgagc gtgttcccaa gcatgcacaa gtacctgtgg   600
tggaagaaat acctgacaca ggcccagctg gtgcaatttg tgctgaccat cacccacacc   660
atgagcgccg tggtgaaacc ttgtggattt ccattcggct gcctgatttt ccagtctagc   720
tacatgctga ccctggtcat cctgttcctc aacttctacg tgcagaccta ccggaagaag   780
cccatgaaga aggacatgca ggagcctcct gctggcaagg aagtgaagaa cggcttcagc   840
aaggcttatt tcaccgccgc taatggcgtg atgaacaaga aagcccag                888

SEQ ID NO: 4            moltype = DNA   length = 613
FEATURE                 Location/Qualifiers
source                  1..613
                        mol_type = other DNA
                        organism = Adenovirus
SEQUENCE: 4
ctagttatta atagtaatca attacggggt cattagttca tagcccatat atggagttcc    60
gcgttacata acttacggta aatggcccgc ctggctgacc gcccaacgac ccccgcccat   120
tgacgtcaat aatgacgtat gttcccatag taacgccaat agggactttc cattgacgtc   180
aatgggtgga ctatttacgg taaactgccc acttggcagt acatcaagtg tatcatatgc   240
caagtacgcc ccctattgac gtcaatgacg gtaaatggcc cgcctggcat tatgcccagt   300
acatgacctt atgggacttt cctacttggc agtacatcta cgtattagtc atcgctatta   360
ccatggtgat gcggttttgg cagtacatca atgggcgtgg atagcggttt gactcacggg   420
gatttccaag tctccacccc attgacgtca atgggagttt gttttggcac caaaatcaac   480
gggactttcc aaaatgtcgt aacaactccg ccccattgac gcaaatgggc ggtaggcgtg   540
tacggtggga ggtctatata agcagagctc tctggctaac tagagaaccc actgcttact   600
ggcttatcga aat                                                       613

SEQ ID NO: 5            moltype = DNA   length = 203
FEATURE                 Location/Qualifiers
source                  1..203
                        mol_type = other DNA
                        organism = Adenovirus
SEQUENCE: 5
actctcttcc gcatcgctgt ctgcgagggc cagctgttgg gctcgcggtt gaggacaaac    60
tcttcgcggt ctttccagta ctcttggatc ggaaacccgt cggcctccga acggtactcc   120
gccaccgagg acctgagcg agtccgcatc gaccggatcg gaaaacctct cgagaaaggc   180
gtctaaccag tcacagtcgc aag                                            203

SEQ ID NO: 6            moltype = DNA   length = 306
FEATURE                 Location/Qualifiers
source                  1..306
                        mol_type = other DNA
                        organism = Adenovirus
```

```
SEQUENCE: 6
gtaggctgag caccgtggcg ggcggcagcg ggtggcggtc ggggttgttt ctggcggagg    60
tgctgctgat gatgtaatta aagtaggcgg tcttgagacg gcggatggtc gaggtgaggt   120
gtggcaggct tgagatccag ctgttggggt gagtactccc tctcaaaagc gggcattact   180
tctgcgctaa gattgtcagt ttccaaaaac gaggaggatt tgatattcac ctggcccgat   240
ctggccatac acttgagtga caatgacatc cactttgcct ttctctccac aggtgtccac   300
tcccag                                                              306

SEQ ID NO: 7            moltype = DNA   length = 341
FEATURE                 Location/Qualifiers
source                  1..341
                        mol_type = other DNA
                        organism = Adenovirus
SEQUENCE: 7
ttgtttact tttgtttctg cccttcttcc actgtgacta aatttttgca atatagaaat     60
aatacgggct ttgtgacctt tagcgttttc ttagctctac aaatgttgga aaatggattt    120
tgaaccttag caaacaagct gaaacagttt aaacatttgt ttgtgggtgc agcaatggaa    180
gaaagacttc attggcattt gttatgatgg tgagtacatt tgtgagatta acattctttg    240
ctcaagactg agaggcctct ggtcagccgc ccccattcta aagcaacaca gatcatattc    300
tgtcacactg agatctcagg taactgacct ttctcacatc g                       341

SEQ ID NO: 8            moltype = DNA   length = 242
FEATURE                 Location/Qualifiers
source                  1..242
                        mol_type = other DNA
                        organism = Adenovirus
SEQUENCE: 8
atcgattggc tccggtgccc gtcagtgggc agagcgcaca tcgcccacag tccccgagaa     60
gttggggggga ggggtcggca attgaaccgg tgcctagaga aggtggcgcg gggtaaactg   120
ggaaagtgat gtcgtgtact ggctccgcct ttttcccgag ggtggggggag aaccgtatat    180
aagtgcagta gtcgccgtga acgttctttt tcgcaacggg tttgccgcca gaacacaggt    240
gt                                                                  242

SEQ ID NO: 9            moltype = DNA   length = 81
FEATURE                 Location/Qualifiers
source                  1..81
                        mol_type = other DNA
                        organism = Adenovirus
SEQUENCE: 9
cgcgcgaagc gatcaggcag cggggcgaca aatttcagcc ttctgaaaca agcaggcgac     60
gtggaagaaa accccggtcc a                                              81

SEQ ID NO: 10           moltype = DNA   length = 798
FEATURE                 Location/Qualifiers
source                  1..798
                        mol_type = other DNA
                        organism = Adenovirus
SEQUENCE: 10
atggtgtcca agggcgagga actgttcacc ggcgtggtgc caatcctggt cgagctggac     60
ggcgatgtga atggccacaa gttttctgtg tctggcgaag gcgagggaga tgccacatac    120
ggcaagctga ccctgaagtt catctgcacc acaggaaagt tgcctgtgcc ctggcctacc    180
ctggtgacca ccctcaccta cggcgttcag tgcttcagca gatacccga tcacatgaaa     240
cagcacgact tttttcaagtc cgccatgcct gagggctacg tgcaggagcg gaccatcttc    300
ttcaaagacg acggcaacta caagacaaga gccgaggtga agttcgaggg cgacaccctt    360
gtgaacagaa tcgagctgaa aggcatcgac ttcaaggaag atggaaatat cctgggccac    420
aagctggaat acaactacaa cagccacaac gtgtacatca tggccgacaa gcagaagaac    480
ggcatcaagg tgaacttcaa gatcagacac aacatcgagg acggcagcgt gcagctggcc    540
gatcactacc agcagaacac ccctatcggc gacggccctg tgctgctgcc tgacaaccac    600
tacctgagca cacagagcgc cctgtctaag gaccccaacg agaagagaga tcacatggtc    660
ctgctggaat tcgtgacagc cgctggcata acactcggca tggacgagct gtacaagagc    720
ggcctgagaa gccgggccca ggccagcaac agcgccgtgg acggtacagc cggccccggc    780
tctaccggca gcagatag                                                 798

SEQ ID NO: 11           moltype = DNA   length = 411
FEATURE                 Location/Qualifiers
source                  1..411
                        mol_type = other DNA
                        organism = Adenovirus
SEQUENCE: 11
tcctgttaat caacctctgg attacaaaat ttgtgaaaga ttgactgata ttcttaacta     60
tgttgctcct tttacgctgt gtggatatgc tgctttaatg cctctgtatc atgctattgc    120
ttcccgtacg gctttcgttt tctcctcctt gtataaatcc tggttgctgt ctctttatga    180
ggagttgtgg cccgttgtcc gtcaacgtgg cgtggtgtgc tctgtgtttg ctgacgcaac    240
ccccactggc tggggcattg ccaccacctg tcaactcctt tctgggactt tcgctttccc    300
cctccctatc gccacggcag aactcatcgc cgcctgcctt gcccgctgct ggacaggggc    360
taggttgctg ggcactgata attccgtggt gttgtcgggg aagctgacgt c            411

SEQ ID NO: 12           moltype = DNA   length = 203
FEATURE                 Location/Qualifiers
```

-continued

```
source                    1..203
                          mol_type = other DNA
                          organism = Adenovirus
SEQUENCE: 12
ctgcccgggt ggcatccctg tgacccctcc ccagtgcctc tcctggccct ggaagttgcc   60
actccagtgc ccaccagcct tgtcctaata aaattaagtt gcatcatttt gtctgactag  120
gtgtccttct ataatattat gggggtggagg ggggtggtat ggagcaaggg gcccaagttg  180
ggaagaaacc tgtagggcct gcg                                          203

SEQ ID NO: 13           moltype = DNA  length = 4068
FEATURE                 Location/Qualifiers
source                  1..4068
                        mol_type = other DNA
                        organism = Adenovirus
SEQUENCE: 13
gcgcgctcgc tcgctcactg aggccgcccg ggcaaagccc gggcgtcggg cgacctttgg   60
tcgcccggcc tcagtgagcg agcgagcgcg cagagaggga gtggccaact ccatcactag  120
gggttccttg tagttaatga ttaacggatc tttacaaatt caagccaggt gattcaaca  180
aattttgctg acgatttagg cgcactatcc cctaaactac aaaattagaaa atagcgttcc  240
ttgacactag ttattaatag taatcaatta cggggtcatt agttcatagc ccatatatgg  300
agttccgcgt tacataactt acggtaaatg gcccgcctgg ctgaccgccc aacgaccccc  360
gcccattgac gtcaataatg acgtatgttc ccatagtaac gccaataggg actttccatt  420
gacgtcaatg ggtggactat ttacggtaaa ctgcccactt ggcagtacat caagtgtatc  480
atatgccaag tacgccccct attgacgtca atgacggtaa atggcccgcc tggcattatg  540
cccagtacat gaccttatgg gactttccta cttggcagta catctacgta ttagtcatcg  600
ctattaccat ggtgatgcgg ttttggcagt acatcaatgg gcgtggatag cggtttgact  660
cacggggatt tccaagtctc caccccattg acgtcaatgg gagtttgttt tggcaccaaa  720
atcaacggga ctttccaaaa tgtcgtaaca actccgcccc attgacgcaa atgggcggta  780
ggcgtgtacg gtgggaggtc tatataagca gagctctctg gctaactaga aacccactg  840
cttactggct tatcgaaata agctttctca ggggacagct cgtttagtga accgtcagat  900
cctcactctc ttccgcatcg ctgtctgcga gggccagctg ttgggctcgc ggttgaggac  960
aaactcttcg cggtctttcc agtactcttg gatcggaaac ccgtcggcct ccgaacggta  1020
ctccgccacc gagggacctg agcgagtccg catcgaccgg atcggaaaac ctctcgagaa  1080
aggcgtctaa ccagtcacag tcgcaaggta ggctgagcac cgtggcgggc ggcagcgggt  1140
ggcggtcggg gttgtttctg gcggaggtgc tgctgatgat gtaattaaag taggcggtct  1200
tgagacggcg gatggtcgag gtgaggtgtg gcaggcttga gatccagctg ttggggtgag  1260
tactccctct caaaagcggg cattacttct gcgctaagat tgtcagtttc caaaaacgag  1320
gaggatttga tattcacctg gcccgatctg gccatacact tgagtgacaa tgacatccac  1380
tttgcctttc tctccacagg tgtccactcc caggtccaag tttaaacgcc gccaccatgg  1440
aacacctgaa ggcattcgac gacgagatca acgccttcct ggataacatg ttcggaccta  1500
gagatagcag agtgcggggc tggttcatgc tggacagcta cctgcctacc ttcttcctga  1560
cagtgatgta cctgctgtct atctggctgg gcaacaagta catgaaaaat agacctgccc  1620
tgagcctgcg gggcatcctc acactgtaca acctgggaat caccctgctg agcgcctaca  1680
tgctggccga gctgatcctg tcaacatggg agggcggcta caacctgcag tgccaggacc  1740
tgacctctgc cggcgaggcc gacatcagag tggccaaggt gctgtggtgg tactactttt  1800
ctaagagcgt ggaattcctg gacaccatct tcttcgtgct gagaaagaag accagccaga  1860
tcacattcct gcacgtgtac caccacgcca gcatgttcaa catctggtgg tgcgtgctga  1920
actggatccc ctgcggccag agcttttttcg gccctacact gaacagcttc atccacatcc  1980
tgatgtacag ctattacggc ctgagcgtgt ccccagcat gcacaagtac ctgtggtgga  2040
agaaatacct gacacaggcc cagctggtgc aatttgtgct gaccatcacc cacaccatga  2100
gcgccgtggt gaaaccttgt ggatttccat tcggctgcct gatttccag tctagctaca  2160
tgctgacccct ggtcatcctg ttcctcaact tctacgtgca gacctaccgg aagaagccca  2220
tgaagaagga catgcaggag cctcctgctg gcaaggaagt gaagaacggc ttcagcaagg  2280
cttatttcac cgccgctaat ggcgtgatga acaagaaagc ccagcgcgcg aagcgatcag  2340
gcagcggggc gacaaatttc agccttctga aacaagcagg cgacgtggaa gaaaacccg  2400
gtccaatggt gtccaagggc gaggaactgt tcaccggcgt ggtgccaatc ctggtcgagc  2460
tggacggcga tgtgaatggc cacaagtttt ctgtgtctgg cgaaggcgag ggagatgcca  2520
catacggcaa gctgacccctg aagttcatct gcaccacagg aaagttgcct gtgccctggc  2580
ctaccctggt gaccacccctc acctacggcg ttcagtgctt cagcagatac cccgatcaca  2640
tgaaacagca cgactttttc aagtccgcca tgcctgaggg ctacgtgcag gagcggacca  2700
tcttcttcaa agacgacggc aactacaaga agagccga ggtgaagttc gagggcgaca  2760
cccttgtgaa cagaatcgag ctgaaaggca tcgacttcaa ggaagatgga aatatcctgg  2820
gccacaagct ggaatacaac tacaacagcc acaacgtgta tcatcatgcc gacaagcaga  2880
agaacggcat caaggtgaac ttcaagatca gacacaacat cgaggtgaac agcgtgcag  2940
tggccgatca ctaccagcag aacaccccta tcggcgacgg ccctgtgctg ctgcctgaca  3000
accactacct gagcacacag agcgccctgt ctaaggaccc caacgagaag agagatcaca  3060
tggtcctgct ggaattcgtg acagccgctg gcataacact cggcatggac gagctgtaca  3120
agagcggcct gagaagccgg gcccaggcca gcaacagcgc cgtggacggt acagccggcc  3180
ccggctctac cggcagcaga tagtcctgtt aatcaacctc tggattacaa aatttgtgaaa  3240
agattgactg atattcttaa ctatgttgct cctttacgc tgtgtggata tgctgcttta  3300
atgcctctgt atcatgctat tgcttcccgt acggctttcg ttttctcctc cttgtataaa  3360
tcctggttgc tgtctcttta tgaggagttg tggcccgttg tccgtcaacg tggcgtggtg  3420
tgctctgtgt ttgctgacgc aacccccact ggctggggca ttgccaccac ctgtcaactc  3480
ctttctggga ctttcgcttt cccctccct atcgccacgg cagaactcat cgccgcctgc  3540
cttgcccgc gctggacagg gctaggttg ctgggcactg ataattccgt ggtgttgtcg  3600
gggaagctga cgtcctgccc gggtggcatc cctgtgaccc ctcccagtg cctctcctgg  3660
ccctggaagt tgccactcca gtgcccacca gccttgtcct aataaaatta gttgcatca  3720
ttttgtctga ctaggtgtcc ttctataata ttatgggggtg gaggggggtg gtatggagca  3780
aggggcccaa gttgggaaga aacctgtagg gcctgcgagc gctggctaga attacctacc  3840
```

-continued

```
ggcctccacc ataccttcga tattcgcgcc cactctccca ttaatccgca caagtggatg  3900
tgatgcgatt gcccgctaag atagttaatc attaactaca aggaacccct agtgatggag  3960
ttggccactc cctctctgcg cgctcgctcg ctcactgagg ccgggcgacc aaaggtcgcc  4020
cgacgcccgg gctttgcccg ggcggcctca gtgagcgagc gagcgcgc               4068

SEQ ID NO: 14           moltype = DNA   length = 3571
FEATURE                 Location/Qualifiers
source                  1..3571
                        mol_type = other DNA
                        organism = Adenovirus
SEQUENCE: 14
ctagttatta atagtaatca attacggggt cattagttca tagcccatat atggagttcc  60
gcgttacata acttacggta aatggcccgc ctggctgacc gcccaacgac cccgcccat   120
tgacgtcaat aatgacgtat gttcccatag taacgccaat agggactttc cattgacgtc  180
aatgggtgga ctatttacgg taaactgccc acttggcagt acatcaagtg tatcatatgc  240
caagtacgcc ccctattgac gtcaatgacg gtaaatggcc cgcctggcat tatgcccagt  300
acatgacctt atgggacttt cctacttggc agtacatcta cgtattagtc atcgctatta  360
ccatggtgat gcggttttgg cagtacatca atgggcgtgg atagcggttt gactcacggg  420
gatttccaag tctccacccc attgacgtca atgggagttt gttttggcac caaaatcaac  480
gggactttcc aaaatgtcgt aacaactccg ccccattgac gcaaatgggc ggtaggcgtg  540
tacggtggga ggtctatata agcagagctc tctggctaac tagagaaccc actgcttact  600
ggcttatcga aataagcttt ctcagggaag atctcgttta gtgaaccgtc agatcctcac  660
tctcttccgc atcgctgtct gcgaggggcca gctgttgggc tcgcggttga ggacaaactc  720
ttcgcggtct ttccagtact cttggatcgg aaacccgtcg gcctccgaac ggtactccgc  780
caccgaggga cctgagcgag tccgcatcga ccggatcgga aaacctctcg agaaaggcgt  840
ctaaccagtc acagtcgcaa ggtaggctga gcaccgtgac gggtggcggt  900
cggggttgtt tctggcggag gtgctgctga tgatgtaatt aaagtaggcg gtcttgagac  960
ggcggatggt cgaggtgagg tgtggcaggc ttgagatcca gctgttgggg tgagtactcc  1020
ctctcaaaag cgggcattac ttctgcgcta agattgtcag tttccaaaaa cgaggaggat  1080
ttgatattca cctggcccga tctggccata cacttgagtg acaatgacat ccactttgcc  1140
tttctctcca caggtgtcca ctcccaggtc caagtttaaa cgccgccacc atggaacacc  1200
tgaaggcatt cgacgacgag atcaacgcct tcctggataa catgttcgga cctagagata  1260
gcagagtgcg gggctggttc atgctggaca gctacctgcc taccttcttc ctgacagtga  1320
tgtacctgct gtctatctgg ctgggcaaca agtacatgaa aaatagacct gccctgagcc  1380
tgcggggcat cctcacactg tacaacctgg gaatcaccct gctgagcgcc tacatgctgg  1440
ccgagctgat cctgtcaaca tgggagggcg gctacaacct gcagtgccag gacctgacct  1500
ctgccggcga ggccgacatc agagtggcca aggtgctgtg gtggtactac ttttctaaga  1560
gcgtggaatt cctggacacc atcttcttcg tgctgagaaa gaagaccagc cagatcacat  1620
tcctgcacgt gtaccaccac gccagcatgt tcaacatctg gtggtgcgtg ctgaactgga  1680
tccctgcgg ccagagcttt ttcggcccta cactgaacag cttcatccac atcctgatgt  1740
acagctatta cggcctgagc gtgttcccca gcatgcacaa gtacctgtgg tggaagaaat  1800
acctgacaca ggcccagctg gtgcaatttg tgctgaccat cacccacacc atgagcgccg  1860
tggtgaaacc ttgtggattt ccattcggct gcctgatttt ccagtctagc tacatgctga  1920
ccctggtcat cctgttcctc aacttctacg tgcagaccta ccggaagaag cccatgaaga  1980
aggacatgca ggagcctcct gctggcaagg aagtgaagaa cggcttcagc aaggcttatt  2040
tcaccgccgc taatggcgtg atgaacaaga agcccagcg cgcgaagcga tcaggcagcg  2100
gggcgacaaa tttcagcctt ctgaaacaag caggcgacgt ggaagaaaac ccggtccaa   2160
tggtgtccaa gggcgaggaa ctgttcaccg gcgtggtgcc aatcctggtc gagctggacg  2220
gcgatgtgaa tggccacaag ttttctgtgt ctggcgaagg cgaggagat gccacatacg   2280
gcaagctgac cctgaagttc atctgcacca caggaaagtt gcctgtgccc tggcctaccc  2340
tggtgaccac cctcacctac ggcgttcagt gcttcagcag ataccccgat cacatgaaac  2400
agcacgactt tttcaagtcc gccatgcctg agggctacgt gcaggagcgg accatcttct  2460
tcaaagacga cggcaactac aagacaagag ccgaggtgaa gttcgagggc gacacccttg  2520
tgaacagaat cgagctgaaa ggcatcgact tcaaggaaga tggaaatatc ctgggccaca  2580
agctggaata caactacaac agccacaacg tgtacatcat ggccgacaag cagaagaacg  2640
gcatcaaggt gaacttcaag atcagacaca acatcgagga cggcagcgtg cagctggccg  2700
atcactacca gcagaacacc cctatcggcg acggccctgt gctgctgcct gacaaccact  2760
acctgagcac acagagcgcc ctgtctaagg accccaacga gaagagagat cacatggtcc  2820
tgctggaatt cgtgacagcc gctggcataa cactcggcat ggacgagctg tacaagagcg  2880
gcctgagaag ccgggcccag gccagcaaca gcgccgtgga cggtacagcc ggccccggct  2940
ctaccggcag cagatagtcc tgttaatcaa cctctggatt acaaaatttg tgaaagattg  3000
actgatattc ttaactatgt tgctcctttt acgctgtgtg gatatgctgc tttaatgcct  3060
ctgtatcatg ctattgcttc ccgtacggct ttcgttttct cctccttgta taaatcctgg  3120
ttgctgtctc tttatgagga gttgtggccc gttgtccgtc aacgtggcgt ggtgtgctct  3180
gtgtttgctg acgcaacccc cactggctgg ggcattgcca ccacctgtca actcctttct  3240
gggactttcg ctttccccct ccctatcgcc acggcagaac tcatcgccgc ctgccttgcc  3300
cgctgctgga caggggctag gttgctgggc actgataatt ccgtggtgtt gtcggggaag  3360
ctgacgtcct gcccgggtgg catcctgtg acccctcccc agtgcctctc ctggccctgg   3420
aagttgccac tccagtgccc accagccttg tcctaataaa attaagttgc atcattttgt  3480
ctgactaggt gtccttctat aatattatgg ggtggagggg ggtggtatgg agcaaggggc  3540
ccaagttggg aagaaacctg tagggcctgc g                                 3571

SEQ ID NO: 15           moltype = DNA   length = 295
FEATURE                 Location/Qualifiers
source                  1..295
                        mol_type = other DNA
                        organism = Adenovirus
SEQUENCE: 15
gggcccaga agcctggtgg ttgtttgtcc ttctcagggg aaaagtgagg cggcccttg    60
```

```
gaggaagggg ccgggcagaa tgatctaatc ggattccaag cagctcaggg gattgtcttt   120
ttctagcacc ttcttgccac tcctaagcgt cctccgtgac cccggctggg atttagcctg   180
gtgctgtgtc agccccgggc tcccaggggc ttcccagtgg tccccaggaa ccctcgacag   240
ggccagggcg tctctctcgt ccagcaaggg cagggacggg ccacaggcca agggc         295

SEQ ID NO: 16          moltype = DNA  length = 3544
FEATURE                Location/Qualifiers
source                 1..3544
                       mol_type = other DNA
                       organism = Adenovirus
SEQUENCE: 16
gcgcgctcgc tcgctcactg aggccgcccg ggcaaagccc gggcgtcggg cgacctttgg   60
tcgcccggcc tcagtgagcg agcgagcgcg cagagaggga gtggccaact ccatcactag   120
gggttccttg tagttaatga ttaacggatc tttacaaatt caagccaggt gatttcaaca   180
aatttttgctg acgatttagg cgcactatcc cctaaactac aaaattagaaa atagcgttcc  240
ttgacactag tttgtttttac ttttgtttct gcccttcttc cactgtgact aaattttttgc  300
aatatagaaa taatacgggc tttgtgacct ttagcgtttt cttagctcta caaatgttgg   360
aaaatggatt ttgaacctta gcaaacaagc tgaaacagtt taaacatttg tttgtgggtg   420
cagcaatgga agaaagactt cattggcatt tgttatgatg gtgagtacat ttgtgagatt   480
aacattcttt gctcaagact gagaggcctc tggtcagccg cccccattct aaagcaacac   540
agatcatatt ctgtcacact gagatctcag gtaactgacc tttctcacat cgactagtct   600
agttattaat agtaatcaat tacggggtca ttagttcata gcccatatat ggagttccgc   660
gttacataac ttacggtaaa tggcccgcct ggctgaccgc ccaacgaccc ccgcccattg   720
acgtcaataa tgacgtatgt tcccatagta acgccaatag ggactttcca ttgacgtcaa   780
tgggtggact atttacggta aactgcccac ttggcagtac atcaagtgta tcatatgcca   840
agtacgcccc ctattgacgt caatgacggt aaatggcccg cctggcatta tgcccagtac   900
atgaccttat gggactttcc tacttggcag tacatctacg tattagtcat cgctattacc   960
atggtgatgc ggttttggca gtacatcaat gggcgtggat agcggtttga ctcacgggga  1020
tttccaagtc tccacccccat tgacgtcaat gggagtttgt tttggcacca aaatcaacgg  1080
gacttcaa aatgtcgtaa caactccgcc ccattgacgc aaatgggcgg taggcgtgta  1140
cggtgggagg tctatataag cagagctctc tggctaacta gagaacccac tgcttactgg  1200
cttatcgaaa taagcttct caggggagat ctcgtttagt gaaccgtcag atcctcactc  1260
tcttccgcat cgctgtctgc gagggccagc tgttgggctc gcggttgagg acaaactctt  1320
cgcggtcttt ccagtactct tggatcggaa acccgtcggc ctccgaacgg tactccgca  1380
ccgagggacc tgagcgagtc cgcatcgacc ggatcggaaa acctctcgag aaaggcgtct  1440
aaccagtcac agtcgcaagg taggctgagc accggtggcgg gcggcagcgg gtggcggtcg  1500
gggttgtttc tggcggaggt gctgctgatg atgtaattaa agtaggcggt cttgagacgg  1560
cggatggtcg aggtgaggtg tggcaggctt gagatccagc tgttggggtg agtactccct  1620
ctcaaagcg ggcattactt ctgcgctaag attgtcagtt tccaaaaacg aggaggattt  1680
gatattcacc tggcccgatc tggccataca cttgagtgac aatgacatcc actttgcctt  1740
tctctccaca ggtgtccact cccaggtcca agtttaaacg ccgccaccat ggaacacctg  1800
aaggcattcg acgacgagat caacgccttc ctggataaca tgttcggacc tagagatagc  1860
agagtgcggg gctggttcat gctggacagc tacctggccta ccttcttcct gacagtgatg  1920
tacctgctgt ctatctggct gggcaacaag tacatgaaaa atagacctgc cctgagcctg  1980
cggggcatcc tcacactgta caacctggga atcaccctgc tgagcgccta catgctggcc  2040
gagctgatcc tgtcaacatg ggagggcggc tacaacctgc agtgccagga cctgacctct  2100
gccggcgagg ccgacatcag agtggccaag gtgctgtggt ggtactactt ttctaagagc  2160
gtggaattcc tggacaccat cttcttcgtg ctgagaaaga agaccagcca gatcacattc  2220
ctgcacgtgt accaccacgc cagcatgttc aacatctggt ggtgcgtgct gaactggatc  2280
ccctgcggcc agagcttttt cggcctaca ctgaacagct tcatccacat cctgatgtac  2340
agctattacg gctgagcgt gttccccagc atgcacaagt acctgtggtg gaagaaatac  2400
ctgacacagg cccagctggt gcaatttgtg ctgaccatca cccacaccat gagcgccgtg  2460
gtgaaacctt gtggatttcc attcggctgc ctgattttcc agtctagcta catgctgacc  2520
ctggtcatcc tgttcctcaa cttctacgtg cagacctacc ggaagaagcc catgaagaag  2580
gacatgcagg agcctcctgc tggcaaggaa gtgaagaacg gcttcagcaa ggcttatttc  2640
accgccgcta atggcgtgat gaacaagaaa gcccagtagt cctgttaatc aacctctgga  2700
ttacaaaatt tgtgaaagat tgactgatat tcttaactat gttgctcctt ttacgctgtg  2760
tggatatgct gctttaatgc ctctgtatca tgctattgct tcccgtacgg ctttcgtttt  2820
ctcctccttg tataaatcct ggttgctgtc tctttatgag gagttgtggc ccgttgtccg  2880
tcaacgtggc gtggtgtgct ctgtgtttgc tgacgcaacc cccactggct ggggcattgc  2940
caccacctgt caactccttt ctgggacttt cgctttcccc ctccctatcg ccacggcaga  3000
actcatcgcc gcctgccttg cccgctgctg acaggggct aggttgctgg gcactgataa  3060
ttccgtggtg ttgtcgggga agctgacgtc ctgcccgggg ggcatccctg tgacccctcc  3120
ccagtgcctc tcctggccct ggaagttgcc actccagtgc ccaccagcct tgtcctaata  3180
aaattaagtt gcatcatttt gtctgactag gtgtccttct ataatattat ggggtggagg  3240
ggggtggtat ggagcaaggg gccaagttg gaagaaacc tgtagggcct gcgagcgctg  3300
gctagaatta cctaccggcc tccaccatac cttcgatatt cgcgcccact ctcccattaa  3360
tccgcacaag tggatgtgat gcgattgccc gctaagatag ttaatcatta actacaagga  3420
acccctagtg atggagttgg ccactccctc tctgcgcgct cgctcgctca ctgaggccgg  3480
gcgaccaaag gtcgcccgac gcccgggctt tgcccgggcg gcctcagtga gcgagcgagc  3540
gcgc                                                              3544
                                                                   3544

SEQ ID NO: 17          moltype = DNA  length = 3234
FEATURE                Location/Qualifiers
source                 1..3234
                       mol_type = other DNA
                       organism = Adenovirus
SEQUENCE: 17
gcgcgctcgc tcgctcactg aggccgcccg ggcaaagccc gggcgtcggg cgacctttgg   60
```

-continued

```
tcgcccggcc tcagtgagcg agcgagcgcg cagagaggga gtggccaact ccatcactag   120
gggttccttg tagttaatga ttaacggatc tttacaaatt caagccaggt gatttcaaca   180
aattttgctg acgatttagg cgcactatcc cctaaactac aaattagaaa atagcgttcc   240
ttgacactag tttgttttac ttttgtttct gcccttcttc cactgtgact aaattttttgc  300
aatatagaaa taatacgggc tttgtgacct ttagcgtttt cttagctcta caaatgttgg   360
aaaatggatt ttgaacctta gcaaacaagc tgaaacagtt taaacatttg tttgtgggtg   420
cagcaatgga agaaagactt cattggcatt tgttatgatg gtgagtacat ttgtgagatt   480
aacattcttt gctcaagact gagaggcctc tggtcagccg cccccattct aaagcaacac   540
agatcatatt ctgtcacact gagatctcag gtaactgacc tttctcacat cgactagtgc   600
ggccgcgggc cccagaagcc tggtggttgt ttgtccttct caggggaaaa gtgaggcggc   660
cccttggagg aaggggccgg gcagaatgat ctaatcggat tccaagcagc tcaggggatt   720
gtcttttttct agcaccttct tgccactcct aagcgtcctc cgtgacccccg gctgggattt   780
agcctggtgc tgtgtcagcc ccgggctccc aggggcttcc cagtggtccc caggaaccct   840
cgacagggcc agggcgtctc tctcgtccag caagggcagg gacgggccac aggccaaggg   900
caagctttct caggggagat ctcgtttagt gaaccgtcag atcctcactc tcttccgcat   960
cgctgtctgc gagggccagc tgttgggctc gcggttgagg acaaactctt cgcggtcttt  1020
ccagtactct tggatcggaa acccgtcggc ctccgaacgg tactccgcca ccgagggacc  1080
tgagcgagtc cgcatcgacc ggatcggaaa acctctcgga aaaggcgtct aaccagtcac  1140
agtcgcaagg taggctgagc accgtggcgg gcggcagcgg gtggcggtcg gggttgtttc  1200
tggcggaggt gctgctgatg atgtaattaa agtaggcggt cttgagacgg cggatggtcg  1260
aggtgaggtg tggcaggctt gagatccagc tgttgggggtg agtactccct ctcaaaagcg  1320
ggcattactt ctgcgctaag attgtcagtt tccaaaaacg aggaggattt gatattcacc  1380
tggcccgatc tggccataca cttgagtgac aatgacatcc actttgcctt tctctccaca  1440
ggtgtccact cccaggtcca agtttaaacg ccgccaccat ggaacacctg aaggcattcg  1500
acgacgagat caacgccttc ctggataaca tgttcggacc tagagatagc agagtgcggg  1560
gctggttcat gctggacagc tacctgccta ccttcttcct gacagtgatg tacctgctgt  1620
ctatctggct gggcaacaag tacatgaaaa atagacctgc cctgagcctg cggggcatcc  1680
tcacactgta caacctggga atcaccctgc tgagcgccta catgctggcc gagctgatcc  1740
tgtcaacatg ggagggcggc tacaacctgc agtgccagga cctgacctct gccggcgagg  1800
ccgacatcag agtggccaag gtgctgtggt ggtactactt ttctaagagc gtggaattcc  1860
tggacaccat cttcttcgtg ctgagaaaga agaccagcca gatcacattc ctgcacgtgt  1920
accaccacgc cagcatgttc aacatctggt ggtgcgtgct gaactggatc ccctgcggcc  1980
agagcttttt cggccctaca ctgaacagct tcatccacat cctgatgtac agctattacg  2040
gcctgagcgt gttccccagc atgcacaagt acctgtggtg gaagaaatac ctgacacagg  2100
cccagctggt gcaatttgtg ctgaccatca cccacaccat gagcgccgtg gtgaaacctt  2160
gtggatttcc attcggctgc ctgatttttcc agtctagcta catgctgacc ctggtcatcc  2220
tgttcctcaa cttctacgtg cagacctacc ggaagaagcc catgaagaag gacatgcagg  2280
agcctcctgc tggcaaggaa gtgaagaacg gcttcagcaa ggcttatttc accgccgcta  2340
atggcgtgat gaacaagaaa gcccagtagt cctgttaatc aacctctgga ttacaaaatt  2400
tgtgaaagat tgactgatat tcttaactat gttgctcctt ttacgctgtg tggatatgct  2460
gctttaatgc ctctgtatca tgctattgct tcccgtacgg cttttcgtttt ctcctccttg  2520
tataaatcct ggttgctgtc tctttatgag gagttgtggc ccgttgtccg tcaacgtggc  2580
gtggtgtgca ctgtgtttgc tgacgcaacc cccactggtt ggggcattgc caccacctgt  2640
caactccttt ctgggacttt cgctttcccc ctccctatcg ccacggcaga actcatcgcc  2700
gcctgccttg cccgctgctg gacaggggct aggttgctgg gcactgataa ttccgtggtg  2760
ttgtcgggga agctgacgtc ctgcccgggt ggcatccctg tgacccctcc ccagtgcctc  2820
tcctggccct ggaagttgcc actccagtgc ccaccagcct tgtcctaata aaattaagtt  2880
gcatcatttt gtctgactag gtgtccttct ataatattat ggggtggagg gggtggtat   2940
ggagcaaggg gcccaagttg ggaagaaacc tgtagggcct gcgagcgctg ctagaatta   3000
cctaccggcc tccaccatac cttcgatatt cgcgcccact ctcccattaa tccgcacaag  3060
tggatgtgat gcgattgccc gctaagatag ttaatcatta actacaagga acccctagtg  3120
atggagttgg ccactccctc tctgcgcgct cgctcgctca ctgaggccgg cgaccaaag   3180
gtcgcccgac gcccgggctt tgcccgggcg gcctcagtga gcgagcgagc gcgc         3234
```

```
SEQ ID NO: 18          moltype = DNA  length = 3181
FEATURE                Location/Qualifiers
source                 1..3181
                       mol_type = other DNA
                       organism = Adenovirus
SEQUENCE: 18
gcgcgctcgc tcgctcactg aggccgcccg ggcaaagccc gggcgtcggg cgacctttgg   60
tcgcccggcc tcagtgagcg agcgagcgcg cagagaggga gtggccaact ccatcactag   120
gggttccttg tagttaatga ttaacggatc tttacaaatt caagccaggt gatttcaaca   180
aattttgctg acgatttagg cgcactatcc cctaaactac aaattagaaa atagcgttcc   240
ttgacactag tttgttttac ttttgtttct gcccttcttc cactgtgact aaattttttgc  300
aatatagaaa taatacgggc tttgtgacct ttagcgtttt cttagctcta caaatgttgg   360
aaaatggatt ttgaacctta gcaaacaagc tgaaacagtt taaacatttg tttgtgggtg   420
cagcaatgga agaaagactt cattggcatt tgttatgatg gtgagtacat ttgtgagatt   480
aacattcttt gctcaagact gagaggcctc tggtcagccg cccccattct aaagcaacac   540
agatcatatt ctgtcacact gagatctcag gtaactgacc tttctcacat cgactagtgc   600
ggccgcatcg attggctccg gtgcccgtca gtgggcagag cgcacatcgc ccacagtccc   660
cgagaagttg gggggagggg tcggcaattg aaccggtgcc tagagaaggt ggcgcggggt   720
aaactgggaa agtgatgtcg tgtactggct ccgcctttt cccgagggtg ggggagaacc   780
gtatataagt gcagtagtcg ccgtgaacgt tctttttcgc aacgggtttg ccgccagaac   840
acaggtgtaa gctttctcag gggagatctc gtttagtgaa ccgtcagatc ctcactctct   900
tccgcatcgc tgtctgcgag ggccagcgt gggctcgcg gttgaggaca aactcttcgc   960
ggtctttcca gtactcttgg atcggaaacc cgtcggcctc cgaacggtac tccgccaccg  1020
agggacctga gcgagtccgc atcgaccgga tcggaaaacc tctcgagaaa ggcgtctaac  1080
cagtcacagt cgcaaggtag gctgagcacc gtggcgggcg gcagcgggtg gcggtcgggg  1140
```

-continued

```
ttgtttctgg cggaggtgct gctgatgatg taattaaagt aggcggtctt gagacggcgg  1200
atggtcgagg tgaggtgtgg caggcttgag atccagctgt tggggtgagt actccctctc  1260
aaaagcgggc attacttctg cgctaagatt gtcagtttcc aaaaacgagg aggatttgat  1320
attcacctgg cccgatctgg ccatacactt gagtgacaat gacatccact ttgcctttct  1380
ctccacaggt gtccactccc aggtccaagt ttaaacgccg ccaccatgga cacctgaag   1440
gcattcgacg acgagatcaa cgccttcctg gataacatgt tcggacctag agatagcaga  1500
gtgcgggggct ggttcatgct ggacagctac ctgcctacct tcttcctgac agtgatgtac  1560
ctgctgtcta tctggctggg caacaagtac atgaaaaata gacctgccct gagcctgcgg  1620
ggcatcctca cactgtacaa cctgggaatc accctgctga gcgcctacat gctggccgag  1680
ctgatcctgt caacatggga gggcggctac aacctgcagt gccaggacct gacctctgcc  1740
ggcgaggccg acatcagagt ggccaaggtg ctgtggtggt actactttc taagagcgtg  1800
gaattcctgg acaccatctt cttcgtgctg agaaagaaga ccagccagat cacattcctg  1860
cacgtgtacc accacgccag catgttcaac atctggtggt gcgtgctgaa ctggatcccc  1920
tgcggccaga gctttttcgg ccctcacactg aacagcttca tccacatcct gatgtacagc  1980
tattacggcc tgagcgtgtt ccccagcatg cacaagtacc tgtggtggaa gaaatacctg  2040
acacaggccc agctggtgca atttgtgctg accatcaccc acaccatgag cgccgtggtg  2100
aaaccttgtg gatttccatt cggctgcctg attttccagt ctagctacat gctgaccctg  2160
gtcatcctgt tcctcaactt ctacgtgcag acctaccgga agaagcccat gaagaaggac  2220
atgcaggagc ctcctgctgg caaggaagtg aagaacggct tcagcaaggc ttatttcacc  2280
gccgctaatg gcgtgatgaa caagaaagcc cagtagtcct gttaatcaac ctctggatta  2340
caaaatttgt gaaagattga ctgatattct taactatgtt gctcctttta cgctgtgtgg  2400
atatgctgct ttaatgcctc tgtatcatgc tattgcttcc cgtacggctt tcgttttctc  2460
ctccttgtat aaatcctggt tgctgtctct ttatgaggag ttgtggcccg ttgtccgtca  2520
acgtggcgtg gtgtgctctg tgtttgctga cgcaacccc actggctggg cattgccac    2580
cacctgtcaa ctcctttctg ggactttcgc tttcccctc cctatcgcca cggcagaact   2640
catcgccga tgccttgccc gctgctggac aggggctagg ttgctgggca ctgataattc   2700
cgtggtgttg tcggggaagc tgacgtcctg cccgggtggc atccctgtga ccctccccca  2760
gtgcctctcc tggccctgga agttgccact ccagtgccca ccagccttgt cctaataaaa  2820
ttaagttgca tcattttgtc tgactaggtg tccttctata atattatggg tggagggggg  2880
gtggtatgga gcaaggggcc caagttggga agaaacctgt agggcctgcg agcgctggct  2940
agaattacct accggcctcc accataccctt cgatattcgc gcccactctc ccattaatgc  3000
gcacaagtgg atgtgatgcg attgcccgct aagatagtta atcattaact caaggaacc   3060
cctagtgatg gagttggcca ctccctctct gcgcgctcgc tcgctcactg aggccgggc   3120
accaaaggtc gcccgacgcc cgggctttgc ccggcggcc tcagtgagcg agcgagcgcg  3180
c                                                                  3181
```

```
SEQ ID NO: 19          moltype = AA  length = 738
FEATURE                Location/Qualifiers
source                 1..738
                       mol_type = protein
                       organism = Adenovirus
SEQUENCE: 19
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                                738
```

```
SEQ ID NO: 20          moltype = AA  length = 738
FEATURE                Location/Qualifiers
source                 1..738
                       mol_type = protein
                       organism = Adenovirus
SEQUENCE: 20
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYFLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                                738
```

```
SEQ ID NO: 21          moltype = AA  length = 738
FEATURE                Location/Qualifiers
source                 1..738
```

-continued

```
                        mol_type = protein
                        organism = Adenovirus
SEQUENCE: 21
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTTTGQNNN SNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRFLTRNL                                                 738

SEQ ID NO: 22           moltype = AA  length = 738
FEATURE                 Location/Qualifiers
source                  1..738
                        mol_type = protein
                        organism = Adenovirus
SEQUENCE: 22
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYFLSR TQTTGGTANT QTLGFSQGGP NTMANQAKNW   480
LPGPCYRQQR VSTTTGQNNN SNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRFLTRNL                                                 738
```